US007959791B2

(12) United States Patent
Kjaer et al.

(10) Patent No.: US 7,959,791 B2
(45) Date of Patent: *Jun. 14, 2011

(54) ENZYME SENSOR WITH A COVER MEMBRANE LAYER COVERED BY A HYDROPHILIC POLYMER

(75) Inventors: Thomas Kjaer, Ballerup (DK); Lydia Dahl Clausen, Lynge (DK)

(73) Assignee: Radiometer Medical APS, Bronshoj (DK)

( * ) Notice: Subject to any disclaimer, the term of this patent is extended or adjusted under 35 U.S.C. 154(b) by 1122 days.

This patent is subject to a terminal disclaimer.

(21) Appl. No.: 11/434,250

(22) Filed: May 16, 2006

(65) Prior Publication Data
US 2006/0275857 A1 Dec. 7, 2006

Related U.S. Application Data

(60) Provisional application No. 60/754,279, filed on Dec. 29, 2005.

(30) Foreign Application Priority Data

May 17, 2005 (DK) .................................. 2005 00718
Jul. 18, 2005 (DK) .................................. 2005 01067

(51) Int. Cl.
*G01N 27/327* (2006.01)
(52) U.S. Cl. ..................................... 205/778; 204/403.06
(58) Field of Classification Search ............ 204/403.01, 204/403.05, 403.06; 205/777.5, 778
See application file for complete search history.

(56) References Cited

U.S. PATENT DOCUMENTS

| 4,169,817 A | 10/1979 | Weber ............................ 510/321 |
| 4,467,811 A * | 8/1984 | Clark, Jr. ....................... 205/778 |
| 5,322,063 A * | 6/1994 | Allen et al. .................... 600/347 |
| 5,326,449 A * | 7/1994 | Cunningham ............ 204/403.09 |
| 5,397,451 A | 3/1995 | Senda et al. .................. 204/403 |
| 5,711,861 A | 1/1998 | Ward et al. |
| 6,099,804 A * | 8/2000 | Clausen et al. .......... 204/403.09 |
| 2003/0070548 A1 * | 4/2003 | Clausen .............................. 96/4 |
| 2004/0106166 A1 | 6/2004 | Matsumoto |

FOREIGN PATENT DOCUMENTS

| EP | 0396431 | 11/1990 |
| GB | 2230865 | 10/1990 |
| JP | 6-229973 | 8/1994 |
| WO | WO 2005/033685 | 4/2005 |
| WO | WO 2006/122552 | 11/2006 |
| WO | WO 2006/122553 | 11/2006 |

OTHER PUBLICATIONS

Tsuchida et al, Clinical Chemistry 29/1, pp. 51-55, 1983.*
Database WPI Week 199415 Derwent Publications Ltd., London, GB; AN 1995-101805 XP002399581 & JP 07025776 A (Asahi Medical Co Ltd) Jan. 27, 1995, Abstract.
Sakong et al. "Asymmetric membrane-based potentiometric solid-state ion sensors" Sensors and actuators B 32(2):161-166 (1996).

* cited by examiner

*Primary Examiner* — Kaj K Olsen
(74) *Attorney, Agent, or Firm* — Morgan Lewis & Bockius LLP

(57) ABSTRACT

The present disclosure relates to an improved enzyme sensor comprising a cover membrane layer of a porous polymeric material, the outer surface and pore mouths of at least one face of the porous polymeric material being covered by a hydrophilic polymer. The sensor is useful determining the presence or amount of biological analytes, e.g., glucose, lactate, creatine, creatinine, etc.

23 Claims, 11 Drawing Sheets

-- PRIOR ART --

-- PRIOR ART --

— PRIOR ART —

ENZYME SENSOR WITH A COVER MEMBRANE LAYER COVERED BY A HYDROPHILIC POLYMER

RELATED APPLICATIONS

The present application claims the benefit of Danish application PA 2005/00718 (filed May 17, 2005), Danish application PA 2005/01067 (filed Jul. 18, 2005), and U.S. provisional application 60/754,279 (filed Dec. 29, 2005), each of which is incorporated herein in its entirety by reference.

FIELD OF THE INVENTION

The present invention relates to improved enzyme sensors comprising a cover membrane layer of a porous polymeric material, the outer surface and pore mouths of at least one face of the porous polymeric material being covered by a hydrophilic polymer.

BACKGROUND OF THE INVENTION

Enzyme sensors are sensors where a chemical species to be measured (an analyte) undergoes an enzyme catalysed reaction in the sensor before detection. The reaction between the analyte and the enzyme (for which the analyte is a substrate), or a cascade of enzymes, yields a secondary species which concentration (under ideal conditions) is proportional with or identical to the concentration of the analyte. The concentration of the secondary species is then detected by a transducer, e.g., by means of an electrode.

The enzyme of an enzyme sensor is typically included in a sensor membrane suitable for contacting a fluid sample. Most typically, the enzyme is included in a separate enzyme layer of the sensor membrane, which is separated from the fluid sample by means of a cover membrane. Hence, the analyte is contacted with the enzyme after diffusion through the cover membrane of the sensor, the enzyme/analyte reaction then takes place, and the secondary species then diffuses to the detector part of the sensor, e.g., an electrode, to yield a response related to the analyte concentration.

In an enzyme sensor, the cover membrane should, on the one hand, have a suitable porosity so that the analyte diffuses from the fluid sample to the enzyme layer in a controlled manner, i.e., the diffusion resistance for the analyte should preferably be so that the conversion of the analyte to the secondary species is only limited by the analyte concentration.

On the other hand, the cover membrane should be impermeable or substantially impermeable to proteins on either side of the cover membrane and particularly to the enzyme of the enzyme layer in order to avoid leaching of the enzyme into the fluid sample.

Porous cover membranes useful for enzyme sensors include track-etched membranes (i.e., membranes where discrete, through-going pores are created by atom bombardment followed by etching) and solvent-cast membranes having tortuous pores (i.e., pores formed by connected pore cells). The latter may be prepared by casting the material dissolved in a solvent as a discrete film or in-situ, where the material may comprise a compound that can easily be washed out of the bulk whereby pores are formed.

A conventional, enzyme-based sensor with a track-etched cover membrane has several problems relating to the fact that large molecules (i.e., a molecular weight larger than approximately 1,000 Daltons) are able to diffuse through the pores thereof.

FIGS. 4A and 4B illustrate the problems of cover membranes containing large, track-etched pores for enzyme-based sensors. It can be seen how the enzyme (25) can migrate into the pores of the porous cover membrane (26). The varying degree of filling (27) leads to variations in sensitivity. Sensor linearity can be compromised, e.g., by enzymes penetrating to the outside of the cover membrane (28), or because the analyte in high and low level samples is being degraded by two different enzyme populations (active enzyme at low analyte levels (33) and active enzyme at high analyte levels (32)). From the sample side, blood proteins (31) can enter the pores and precipitate on the pore walls and thereby decrease the diffusion coefficient of the analyte, thus decreasing the sensor sensitivity when measuring blood samples. Moreover, the mere presence of blood proteins in the pores may give rise to blood bias. A further problem relates to the distribution of the analyte in the enzyme layer, especially where track-etched membranes are used.

If the active enzyme from an underlying enzyme layer is able to migrate into or through the porous cover membrane, it may cause different problems. First of all, a loss of enzyme through the cover membrane (29) causes a reduced lifetime of the sensor unit. Secondly, if the enzyme migrates into the pores of the membrane (27), it will cause varying sensor-to-sensor sensitivity. Furthermore, the sensitivity of the sensor also tends to vary over the first few days until the precipitation/dissolution has come to equilibrium. Such changes are unwanted because they cause variations in sensor performance. If the enzyme precipitates on the outside of the membrane (28), the enzyme will be able to carry out its enzymatic action in the fluid sample. However, in such instances, the amount of analyte (e.g., glucose, lactate, creatine, creatinine) being converted to the secondary species (e.g., $H_2O_2$) is not linearly correlated to the concentration of primary analyte, since other factors such as $K_m$ and the concentration of other possible substrates (e.g., $O_2$) also influence the conversion rate.

If proteins (e.g., blood proteins) from the fluid sample are able to pass into the pores (31) of the cover membrane, the proteins will remain in the liquid column of the pores and thus lower the area and increase the diffusion length for the analyte into the enzyme layer. Therefore, the sensor will have varying sensitivities for the analyte of fluid samples with varying protein content. This phenomenon is referred to as blood bias which is caused by the blood components occupying the pores of the cover membrane, thereby providing a higher (however varying) effective diffusion resistance in the pores of the cover membrane, and, thus, of the enzyme membrane as such.

Moreover, if the surface of the pores is not totally blood compatible, then the proteins may precipitate on the membrane surface including inside the pores (30) and cause a gradually smaller area (gradually reduced effective pore size) for the analyte to diffuse through into the enzyme layer. This phenomenon is referred to as blood drift which is caused by blood components (in particular, proteins and lipids) precipitating on the inner surface of the pores, and, thus, decreasing sensitivity.

Both these effects (blood bias and blood drift) are especially undesirable for sensors in blood analysers because the known enzyme sensors often are calibrated with aqueous liquids, whereas they are meant to measure blood samples.

Conventional solvent-cast membranes also cause problems of the type described above, such as sensor-variability, linearity, unsatisfactory analyte distribution in the enzyme layer, etc.

Moreover, as it is desirable to use effective rinsing solutions for enzyme sensors, in particular rinsing solutions comprising proteases (e.g., subtilisin). It is also important that such proteases are not able to penetrate into the enzyme layer.

U.S. Pat. No. 4,919,767 discloses an enzyme sensor comprising an enzyme layer and a liquid membrane of a porous material filled with liquid having the ability to let the analyte pass while rejecting other species of the samples.

U.S. Pat. No. 6,413,393 discloses a sensor comprising at least one functional coating layer that includes a UV-absorbing polymer, e.g., a polyurethane, a polyurea or a polyurethane/polyurea copolymer including variants comprising hydrophilic segments such as poly(alkylene glycol) and poly(alkylene oxide). The sensor may comprise an enzyme layer and two functional layers, e.g., an analyte limiting layer and a biocompatible layer.

US Published Application 2003/0217966 A1 discloses an implantable membrane for regulating the transport of analytes therethrough that includes a polyurethane (in particular, a polyether urethaneurea) matrix having a network of microdomains of another polymer which may be of the same type, i.e., a polyether urethaneurea.

U.S. Pat. No. 6,652,720 B1 discloses an electrochemical sensor having at least one electrode and a composite membrane. The composite membrane comprises a diffusion-controlling outer layer comprising a polyurethane-based compound, e.g., a mixture of polyurethanes with different water-uptake properties.

US Published Application 2002/065332 A1 discloses a polymeric reference electrode membrane comprising a porous polymer or a hydrophilic plasticizer in combination with a lipophilic polymer e.g., a polyurethane.

U.S. Pat. No. 6,350,524 B1 discloses a solid-state membrane for a chloride-selective electrode comprising an insoluble metal salt layer and a protecting membrane formed of hydrophilic polyurethane.

U.S. Pat. No. 6,200,772 B1 discloses a sensor device having a membrane comprising a polyurethane modified with a non-ionic surfactant, e.g., an aliphatic polyether.

U.S. Pat. No. 5,322,063 A discloses a homogeneous membrane of a hydrophilic polyurethane composition. The membrane is useful for glucose enzyme sensors.

WO 2003/076648 A1 discloses a planar, thick-film biosensor having a homogeneous layer of a polymer (e.g., an aliphatic polyether urethane) comprising an enzyme and a mediator.

US Published Application 2004/0154933 A1 discloses a polymeric membrane for use in electrochemical sensors. The membrane contains carboxylated polyvinyl chloride, e.g., mixed with a polyurethane.

WO 2004/062020 A2 discloses a gas diffusion layer of a porous polymeric material, e.g., a foam, for a fuel cell. The material may be a polyurethane foam or polyether polyurethane foam. Similarly, US 2004/0001993 A1 discloses a gas diffusion layer for fuel cells.

EP 1 486 778 A2 discloses an electrochemical biosensor comprising a membrane of a polymer having a bio-active agent, e.g., an enzyme, entrapped therein.

WO 92/04438 A1 discloses an electrochemical biosensor having a substrate-limiting layer of a hydrophobic plastic layer, e.g., a polyurethane layer.

EP 0 025 110 A2 discloses an electrochemical sensor having an asymmetric semipermeable membrane of, e.g., polyvinyl chloride.

US Published Application 2004/0011671 A1 discloses an implantable device having an enzyme layer, a bioprotective membrane e.g., a polyurethane layer, and an outer angiogenic layer, e.g., of PTFE, PVF, cellulose esters, PVC, polypropylene, polysulfones or poly(methyl methacrylate).

WO 90/05910 A1 discloses a wholly microfabricated biosensor comprising an enzyme layer and an "analyte attenuation layer", e.g., a polyurethane layer.

WO 96/26668 A1 discloses an implantable sensor system comprising a flexible capillary membrane which may be coated with a polyurethane or silicone, wherein said capillary membrane is connected to a channel in contact with an enzyme sensor e.g., a glucose sensor.

U.S. Pat. No. 5,523,118 discloses a microporous membrane for transdermal drug delivery patches. The microporous membrane may be made from, e.g., polyvinyl chloride and is coated with a substantially porous coating formed from an adhesive-compatible urethane-based polymer, e.g., an aliphatic polyether urethane dispersion. The urethane-based polymer coats the surface of the microporous membrane, but does not block the pores thereof.

U.S. Pat. No. 6,509,148 discloses biosensors utilizing a hydrophilic polyurethane mixed with an enzyme.

JP 2655727 B2 discloses an enzyme sensor having a substrate limiting layer of polyurethane or cellulose acetate, or a dual layer of these, and an outer biological-body compatible film of polyvinyl alcohol (PVOH).

In view of the above, there is still a need for improved enzyme sensors having cover membranes providing an efficient barrier for enzymes and other proteins and secondary analytes and yet providing excellent and stable diffusion control of the primary analyte to the enzyme layer.

SUMMARY OF THE INVENTION

It has been found that the present invention reduces or even eliminates at least some or all of the above-mentioned problems associated with known enzyme sensors by providing an enzyme sensor for determining the concentration of an analyte in a fluid sample, said sensor comprising an electrode, at least one enzyme layer and a cover membrane layer for said at least one enzyme layer, wherein the cover membrane comprises at least one porous polymeric material, and wherein the outer surface and pore mouths of at least one face of the at least one porous polymeric material is covered by a hydrophilic polymer. Exemplary hydrophilic polymers include hydrophilic polyurethanes and hydrophilic poly(meth)acrylates.

Moreover, when, for example, hydrophilic polyurethanes and hydrophilic poly(meth)acrylates are used to cover the outer surface and pore mouths of the at least one porous polymeric material, it is possible to tailor the diffusion properties of the hydrophilic polymer to obtain the desired diffusion restriction to make the enzyme membrane suitable for different sample analyte concentration ranges, depending on the different porosities of the porous polymeric material.

Apart from the above-mentioned improvements, it has also been found that sensors having the described cover membrane allow for cleaning with liquids comprising proteases, whereas known sensors typically require cleaning liquids without proteases.

The present invention also provides novel membranes and a method of cleaning the cover membrane of the described enzyme sensors.

BRIEF DESCRIPTION OF THE DRAWINGS

The following figures are merely exemplary embodiments of the invention and are in no way intended to limit the scope of the disclosure.

DETAILED DESCRIPTION OF THE INVENTION

As described herein, the present invention provides a novel enzyme sensor for determining the concentration of an analyte in a fluid sample.

As defined herein, the term "enzyme sensor" is generally intended to encompass electrochemical sensors comprising an enzyme (or an enzyme cascade) which is capable of converting an analyte of interest into a secondary species. The analyte of interest is a possible constituent of the fluid sample, i.e., the enzyme sensor is typically used for determining the concentration of the analyte in the fluid sample. The "analyte" is also sometimes referred to herein as an "enzyme substrate", or simply a "substrate".

The sensors of the invention are typically multi-use sensors. A multi-use sensor is to be understood as a sensor which is used for more than one measurement and, thus, is exposed to more than one volume of sample and may possibly have intermittent contact with calibration liquids, cleaning liquids, etc. Such sensors are typically used for a longer period of time. Thus, the above-mentioned problems, e.g., life-time, sample-to-sample sensitivity due to enzyme migration, blood drift, blood bias, etc. will be particularly predominant in known multi-use sensors. For single use sensors, the present invention will solve or alleviate the problems of blood bias, analyte distribution, etc.

The fluid sample can in principle be any liquid which is compatible with the sensor, and in particular, with the cover membrane. In an exemplary embodiment, the fluid sample is an aqueous liquid. Fluid samples include physiological fluids, such as, for example, urine, saliva, interstitial fluids, spinal fluid and blood. Blood includes whole blood samples, diluted blood samples, blood fractions, pre-reacted blood samples, etc. The sensors are particularly well-suited for whole blood samples.

The sensors of the invention may be of the conventional type or of the planar type, e.g., a thick-film sensor or a thin-film sensor. The enzyme membranes of such sensors are often layered structures and are referred to as layered membranes.

In case of enzyme sensors of the conventional type, a membrane, e.g., a multi-layered membrane comprising, for example, a support layer, an enzyme layer, and a cover membrane, is typically assembled as a discrete object which is then arranged in conjunction with (i.e., generally mounted on the tip of) an electrode. See, e.g., FIG. 1. Methods for the construction of such a multi-layered membrane are well-known in the art. See, e.g., WO 98/21356. Enzyme sensors of the conventional type may include track-etched membranes as well as solvent-cast membranes.

Figure 3:
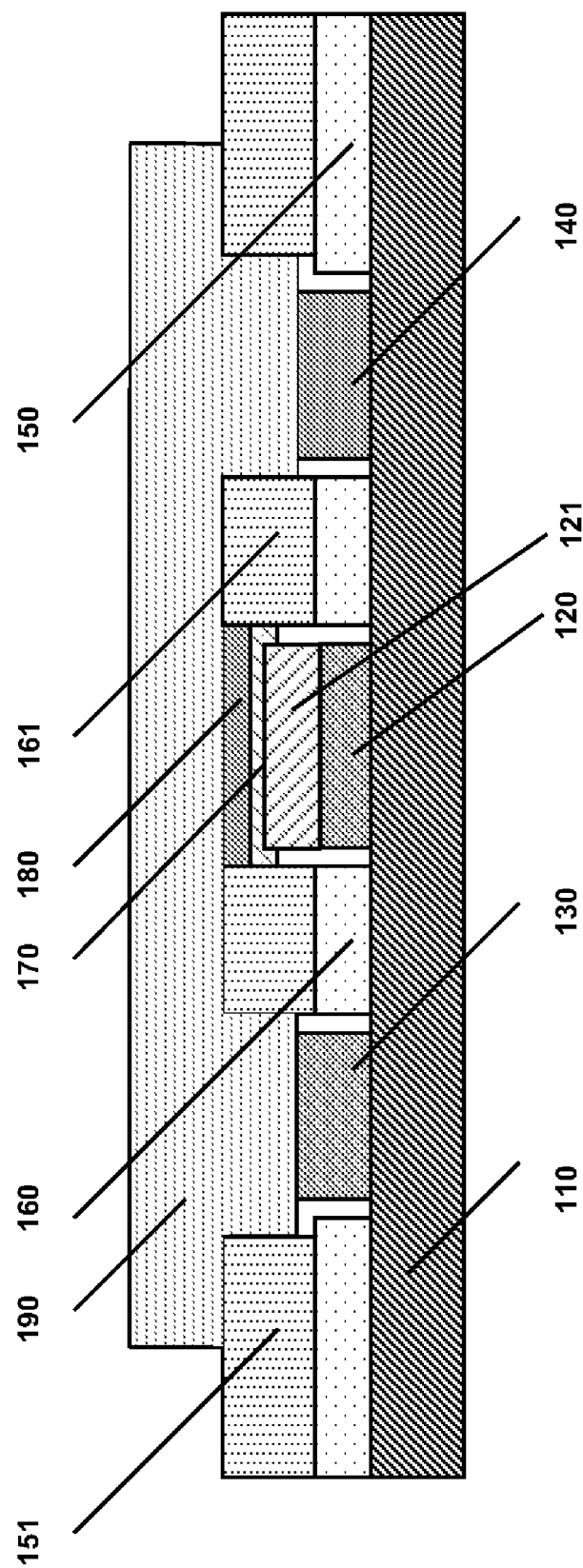
FIG. 3 illustrates an exemplary planar, thick-film sensor construction.

In the case of enzyme sensors of the planar type, e.g., thick-film sensors and thin-film sensors, the electrode and the enzyme membrane comprising the enzyme layer and the cover membrane may be arranged by depositing materials (typically sequentially and individually) corresponding to the electrode, any spacer layer and intermediate layer(s), the enzyme layer, the at least one porous polymeric material and a hydrophilic polymer onto a solid, dielectric substrate, e.g., a ceramic or wafer material. An example of a planar sensor construction is illustrated in FIG. 3. Methods for the construction of planar type sensors, e.g., thick-film sensors and thin-film sensors, are well-known in the art. See, e.g., WO 01/90733, WO 01/65247 and WO 90/05910. The materials corresponding to the layers of such sensor membranes are most often deposited by solvent-casting.

The enzyme sensors of the invention comprise an electrode, at least one enzyme layer and a cover membrane layer for said at least one enzyme layer, wherein the cover membrane comprises at least one porous polymeric material, and wherein the outer surface and pore mouths of at least one face of the at least one porous polymeric material is covered by a hydrophilic polymer. Exemplary hydrophilic polymers include hydrophilic polyurethanes and hydrophilic poly(meth)acrylates.

Cover Membrane

The cover membrane of the enzyme sensor plays an important role in the quality of the enzyme sensor, e.g., by ensuring that a limited, well-defined, representative amount of the analyte is allowed to diffuse into the enzyme layer, i.e., under controlled conditions. Such an analyte-limited conversion is a prerequisite for obtaining a substantially linear relation between the sensor response and the analyte concentration within a reasonable range.

Thus, the enzyme sensors of the invention comprise a diffusion limiting layer in the form of a cover membrane which is adapted to separate the enzyme layer from the fluid sample. The cover membrane is a porous membrane which limits the diffusion of the analyte into the enzyme layer so that the capacity of the immobilised enzyme for conversion of the analyte is not exceeded, and so that sufficient oxygen ($O_2$) for the enzymatic conversion of the analyte is present in the enzyme layer. The principle of diffusion limiting layers is described in, for example, Danish Patent No. 170103.

It is furthermore desirable that the diffusion of the analyte through the cover membrane is invariable over time and from sample to sample, so that an identical analyte concentration for two separate fluid samples gives rise to a well-defined sensor response. Also desirable is the feature that the cover membrane is capable of allowing fast diffusion of a small amount of the analyte across the membrane, thus facilitating an even dispersion of the analyte in the enzyme layer so that an enzyme of the enzyme layer immediately converts the analyte to a secondary species, giving rise to a rapid sensor response. Such an almost simultaneous conversion of the analyte by the enzyme results in an improved linearity. Moreover, it is desirable that the macromolecules, e.g., proteins and enzymes that are present in the fluid sample, are substantially prevented from migrating across the cover membrane. It has been noted that proteases present in e.g., a cleaning solution or a blood sample will have adverse effects on the enzyme layer if such proteases are allowed to migrate into and through the cover membrane.

On the other hand, it is also important that the cover membrane is capable of providing a high retention of the secondary species (e.g., $H_2O_2$ and $O_2$) within the sensor so that the response derived from the secondary species is not biased by substantial amounts of those species diffusing out through the pores of the cover membrane, and so that a sufficient amount of $O_2$ is retained within the enzyme layer in order to maintain analyte limited conversion. These features are particularly relevant to consider if an intermediate layer having a diffusion limiting effect is arranged between the enzyme layer and the electrode (see further below).

A cover membrane possessing several of these favourable characteristics is achieved when the outer surface and pore mouths of at least one face of the at least one porous polymeric material are covered by a hydrophilic polymer that includes, but is not limited to, hydrophilic polyurethanes and hydrophilic poly(meth)acrylates.

The at least one porous polymeric material may be selected from a fairly wide range of materials. Illustrative examples include, but are not limited to, polyesters (such as polyethylene terephthalate (PETP), glycol-modified polyethylene terephthalate (PETG) and glycol-modified polycyclohexylenedimethylene terephthalate (PCTG)), polycarbonates, celluloses (regenerated, acetate, triacetates, acetate butyrates), polyolefins and derivatives thereof, fluorinated hydrocarbon polymers and copolymers (e.g., polychlorotrifluoroethylene, polyvinylidene fluoride, polytetrafluoroethylene, polyethylene chlorotrifluoroethylene, polyethylene tetrafluoroethylene, fluorinated ethylene-propylene copolymer), polyimides (e.g., Kapton), polystyrene, poly(meth)acrylates, polyvinyl chloride and derivatives thereof (including copolymers such as a vinyl chloride-co-(meth)acrylate-type copolymer), polyamides, polyurethanes, polysulphones, polyethersulphones, polyphenylene sulphide, silicones, and copolymers of organosiloxane-polycarbonate (e.g., those disclosed in U.S. Pat. No. 3,189,662).

In an aspect of the invention, the at least one porous polymeric material is selected from polyethylene terephthalate (PETP), polyvinyl chloride, and polycarbonate.

In one embodiment, the porous polymeric material is polyethylene terephthalate (PETP).

In another embodiment, the porous polymeric material is polyvinyl chloride (PVC).

In an exemplary embodiment, the at least one porous polymeric material does not comprise a hydrophilic polyurethane, because it is believed that such a material will provide an excessive level of $H_2O_2$ diffusion, especially if an intermediate layer with a diffusion limiting effect is included.

The cover membrane (and thereby also the at least one porous polymeric material) comprises two faces: one face that is proximal to the enzyme layer and one face that is distal to the enzyme layer, the latter furthermore facing the fluid sample when the enzyme sensor is in use. As mentioned above, at least one face of the at least one porous polymeric material is covered by a hydrophilic polymer.

In an aspect of the invention, at least the face that is distal to the enzyme layer is covered by a hydrophilic polymer. This aspect provides advantages with respect to reduction or even elimination of blood bias and blood drift, and extends the lifetime of the sensor.

In another aspect, at least the face that is proximal to the enzyme layer is covered by a hydrophilic polymer. It is expected that the problems relating to varying sensitivity, lack of linearity, analyte distribution in the enzyme layer and reduced lifetime can be reduced or eliminated in this manner. If the at least one porous polymeric material is properly selected, e.g., by choosing a porous polymeric material that has a suitable blood compatibility, problems relating to blood bias and blood drift may at least in part be reduced, even in the absence of a hydrophilic polymer covering the outer surface and pore mouths of the face of the at least one porous polymeric material that is distal to the enzyme layer.

In an exemplary embodiment, both faces are covered by a hydrophilic polymer. This embodiment provides advantages with respect to reduction or even elimination of blood bias and blood drift, analyte distribution in the enzyme layer, improvement of sensitivity and linearity, extends the lifetime of the sensor, limits the enzyme migration and improves linearity.

Figure 4:
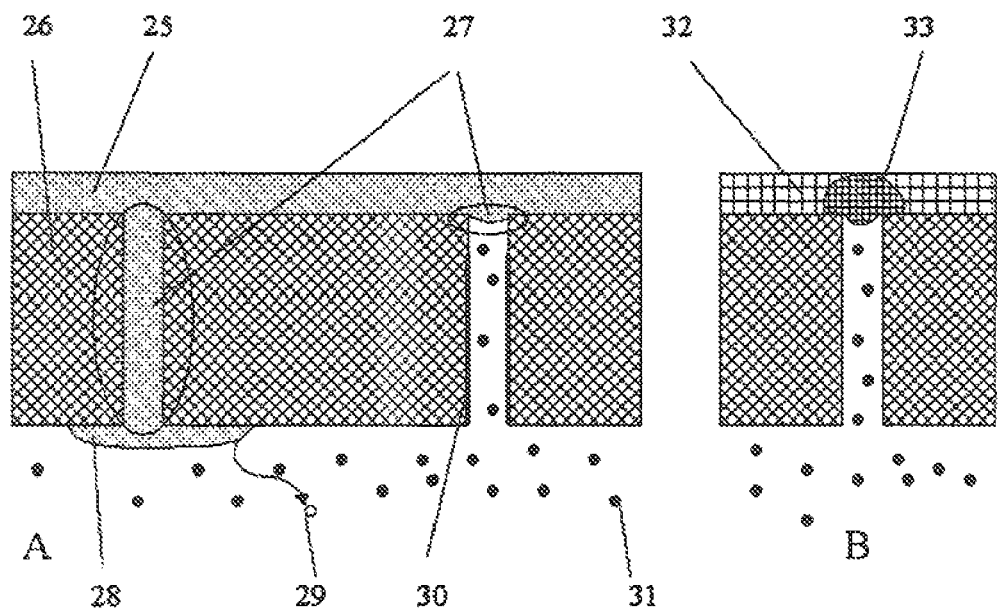
FIGS. 4A and 4B illustrate the problems associated with a conventional enzyme based sensor containing a track-etched membrane.
Figure 5:
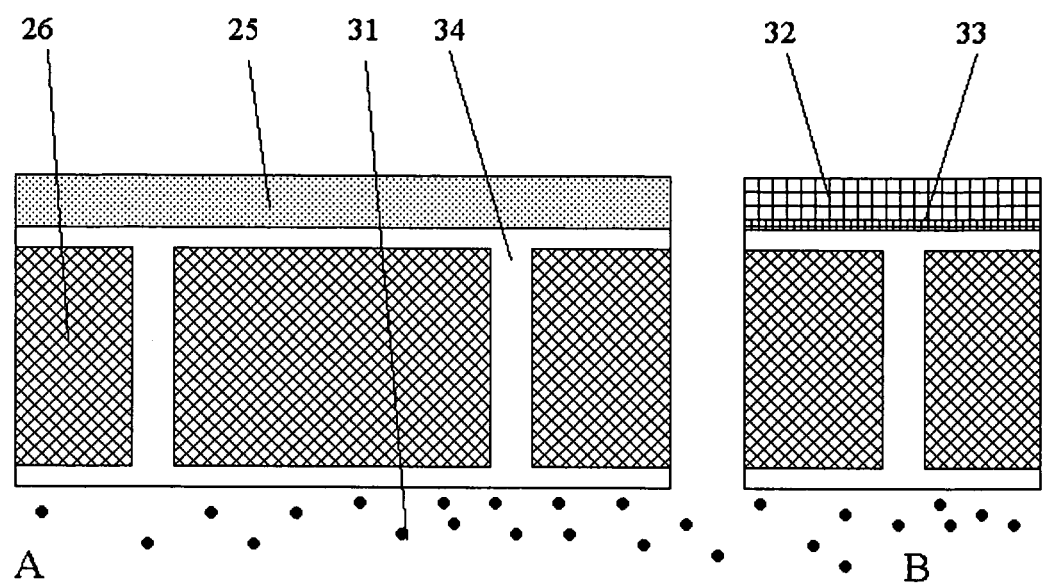
FIGS. 5A and 5B illustrate how a (double-sided) coating of a hydrophilic polymer (such as, but not limited to, a hydrophilic polyurethane or a hydrophilic poly(meth)acrylate) solves the problems associated with a conventional sensor containing a track-etched membrane.

FIGS. 5A and 5B illustrate—as compared to FIGS. 4A and 4B—how a (double sided) coating of a hydrophilic polymer e.g., a hydrophilic polyurethane or a hydrophilic poly(meth)acrylate, solves the problems of a conventional sensor with a track-etched membrane. If the cover membrane is embedded in a layer of a hydrophilic polymer e.g., hydrophilic polyurethane, (34), the above-mentioned problems are all alleviated because large molecules, i.e., enzymes from the enzyme layer and blood proteins or other proteins from the fluid sample, are not able to pass or enter the layer of the hydrophilic polymer.

The expression "outer surface and pore mouths" refers to each of the two faces of the at least one porous polymeric material which represents a surface interrupted by pore mouths (pore openings).

In the present context, the expression "covered by" refers to the fact that not only the surface of the at least one porous polymeric material, but also the pore mouths are covered by the hydrophilic polymer.

The term "a hydrophilic polymer" as used herein is intended to refer to a single hydrophilic polymer as well as a mixture of two or more hydrophilic polymers. It should be understood that the hydrophilic polymer(s) described above may be mixed with up to 30% of other non-hydrophilic polymers. In one preferred embodiment, the coating on the at least one porous polymeric material comprises a hydrophilic polymer selected from hydrophilic polyurethanes and hydrophilic poly(meth)acrylates.

For planar sensors, a coating of the hydrophilic polymer is typically obtained by dispensing, spraying, screen-printing, etc., a solution of the hydrophilic polymer onto the surface (and pore mouths) of the at least one porous polymeric material. In an aspect of the invention, the outer surface and pore mouths of at least one face of the at least one porous polymeric material most distal to the enzyme layer is covered by the hydrophilic polymer. An alternative embodiment, i.e., the one where the enzyme layer is coated with a hydrophilic polymer before establishing the at least one porous polymeric material (and optionally coating the porous polymer material with the same or another hydrophilic polymer) is also envisaged, just as the embodiment where both faces of the at least porous polymer material are coated.

For conventional sensors, a coating on the at least one porous polymeric material may be obtained by dispensing, spraying, screen-printing, etc., a solution of the hydrophilic polymer onto the surface (and pore mounts) of the at least one porous polymeric material (either both faces or just one face thereof), or the at least one porous polymeric material may be submerged into a solution of the hydrophilic polymer, etc.

Hence, in particular for the conventional sensors with track-etched porous materials, both faces of the at least one porous polymeric material may be covered by the hydrophilic polymer. The fact that the face of the at least one porous polymeric material proximal to the enzyme layer also is covered by the hydrophilic polymer is believed to provide particular advantages, in particular for track-etched porous polymeric materials, because a relatively large distance between individual pores gives rise to a non-linear response in the absence of a coating of a hydrophilic polymer. In this situation, the analyte (enzyme substrate) will have to diffuse to non-occupied enzyme molecules within the enzyme layer, and a longer diffusion distance results in a non-simultaneous conversion. In contrast, a coating of the hydrophilic polymer on the face of the at least one porous polymer material proximal to the enzyme layer will facilitate diffusion of the analyte within the layer and provide the analyte more evenly to the enzyme layer, whereby a higher or more linear response is obtained. Thus, in an embodiment where the coating of the hydrophilic polymer on the face of the at least one porous polymer material is proximal to the enzyme layer, the analyte will only have to travel a short distance in the denser enzyme layer until it reaches an available enzyme molecule.

In some aspects of the invention, not only the outer surface and the pore mouths of the at least one porous polymeric material is covered by the hydrophilic polymer, but the hydrophilic polymer has also at least partly penetrated the pores of the porous polymeric material from at least one face thereof.

In these particular embodiments, the at least one porous polymeric material of the cover membrane layer is said to be at least partly impregnated with the hydrophilic polymer.

In the present context, the term "impregnated" is intended to mean that the hydrophilic polymer covers the outer surface and pore mouths of both faces of the at least one porous polymeric material and also has penetrated the pores of the porous polymeric material.

The term "at least partly impregnated" is intended to mean that the hydrophilic polymer covers the outer surface and pore mouths of at least one face of said at least one porous polymeric material and also has at least partly penetrated the pores of the porous polymeric material originating from said at least one face.

In another aspect of the invention, the hydrophilic polymer is substantially insoluble in water upon use of the sensor. However, it should be understood that the hydrophilic polymer is preferably not cross-linked when applied to the cover membrane in order to cover the same, and preferably no subsequent cross-linking takes place. Instead, the combined hydrophilicity and water-insolubility of the hydrophilic polymer is obtained by a suitable combination of hydrophilic segments and hydrophobic segments/moieties of the hydrophilic polymer. This arrangement provides a much simplified procedure of manufacture in that a cross-linking step can be completely omitted.

The term "insoluble in water" is intended to refer to a polymer that does not substantially dissolve in water upon storage of a cover membrane covered by the hydrophilic polymer for 24 hours at 25° C. in an aqueous solution.

In an embodiment of the invention, the at least one porous polymeric material has a porosity in the range of about 0.002 to about 30% (vol/vol).

The desired porosity of the polymeric material depends to a certain extent on the desired upper limit of the detection range. A very high upper limit of the detection range will require a fairly low porosity so as to obtain a broad linear range, such that the cover membrane should present a fairly high diffusion resistance for the analyte. When expressed as a mathematical product of the porosity (% (vol/vol)) and the upper limit of the linear detection range (mM of analyte), the value may be in the range of about 0.01 to about 50 [%(vol/vol)·mM], such as about 0.05 to about 10 [%(vol/vol)·mM] or, such as about 0.1 to about 2 [%(vol/vol)·mM].

In various aspects of the invention, the average pore size of the porous polymeric material is in the range of about 0.05 to about 250 nm, such as about 1 to about 150 nm, or such as about 10 to about 110 nm.

In one embodiment, in particular where the sensor is of the conventional type, the porous polymeric material is a track-etched material, e.g., with a pore density in the range of about 40,000 to about 40,000,000 pores per cm$^2$.

For creatinine/creatine and urea sensors with track-etched cover membranes, the porosity may be in the range of about 0.05 to about –0.1%, such as about 0.2 to about 0.25%. For lactate sensors with track-etched cover membranes, the porosity may be in the range of about 0.0005 to about 0.015%, such as about 0.003 to about 0.004%. For glucose sensors with track-etched cover membranes, the porosity may be in the range of about 0.001 to about 0.05%, such as about 0.01 to about 0.02%. The porosity for track-etched membranes is determined as: porosity (%)=$\pi \times$(pore diameter/2)$^2 \times$(pore density)$\times 100\%$.

The porosity for solvent-cast membranes may more easily be determined as the volume occupied by water when the membrane is wetted with water. The porosity of solvent-cast membranes may be in the range of about 1 to about 40%, such as about 3 to about 30%. The difference of at least one order of magnitude between the porosity of track-etched membranes and solvent-cast membranes can be explained by the fact that only the "effective" pores (i.e. through-going pores) of the track-etched membranes are taken into account, whereas all pores and cavities are included in the determination of porosity for the solvent-cast membranes.

In one embodiment, the hydrophilic polymer is a hydrophilic polyurethane.

Polyurethanes are the most widely used biomedical polymers for blood-contacting surfaces, e.g., for implants and medical devices. Polyurethane elastomers are multiphase block copolymers which consist of alternating blocks of hard and soft segments. Hydrophobic hard segments are formed in the reaction of aliphatic, cycloaliphatic or aromatic diisocyanates with diols, diamines or water. The soft hydrophilic or relative hydrophilic segments are composed of low-molecular weight hydroxy-terminated polyethers, polyesters or aliphatic polyolefins. The hydrophilic polyols are used as chain extenders or can alternatively be incorporated in the prepolymer. Chemical incompatibility between the hard and soft segments and between the hydrophobic and hydrophilic segments, leads to phase segregation in polyurethanes. The hard segment domains, which are interconnected with secondary bonds and dispersed in the soft segment matrix, act as physical cross-links reinforcing the whole system. The soft matrix can be tailored in respect to hydrophilicity by using mixtures of polyethers or polyesters with different hydrophilicities. For very hydrophilic polyurethanes, polyethylene glycol is often used, and the tailoring of their hydrophilic properties can be accomplished with the higher polyalkyl ethers, e.g., polypropylene glycol and polybutylene glycol. In this way, polyurethanes can be produced as hydrophilic, hydrophobic, hydrophilic/hydrophobic, hard and stiff or soft and elastic, hydrolytically stable or deliberately degradable. Because of their hard and soft segmented structure, the polyurethanes are mechanically strong, tear resistant and exhibit good flex life. These properties make the polyurethanes suitable as hydrophilic coatings for sensor membranes. The coatings have high water absorption due to the content of hydrophilic segments and good in-use stability. Due to their pseudo cross-linked segmented structure, the coatings are also insoluble in water. The hydrophilic polyurethane may be selected from polyurethanes having hydrophilic segments included therein, e.g., segments of polyethylene glycol, polypropylene oxide, etc. Such hydrophilic polyurethane may be prepared from polyalkylene glycols (polyalkylene oxides) having terminal hydroxy or amino groups, thereby forming linear polymer chains by reaction with di-isocyanates. Examples of such hydrophilic polyurethanes are those disclosed in U.S. Pat. Nos. 4,789,720; 4,798,876; and 5,563,233. Other suitable examples are polyurethanes modified with hydrophilic groups, e.g., an aliphatic polyether (see, e.g., U.S. Pat. No. 6,200,772 B1).

The hydrophilic segments are typically derived from polyethylene glycols, amino-group terminated polyethylene glycols, polypropylene glycols, amino-group terminated polypropylene glycols, polyethylene oxide, polypropylene oxide, and polyethylene imines, in particular polyethylene glycols.

In some embodiments, the hydrophilic polyurethane is selected from aliphatic polyether urethanes, aliphatic polyether urethaneureas, cycloaliphatic polyether urethanes, cycloaliphatic polyether urethaneureas, aromatic polyether urethanes, aromatic polyether urethaneureas, aliphatic polyester urethanes, aliphatic polyester urethaneureas, cycloaliphatic polyester urethanes, cycloaliphatic polyester urethaneureas, aromatic polyester urethanes, and aromatic polyester urethaneureas. In an exemplary embodiment, aliphatic polyether urethanes or cycloaliphatic polyether urethanes (e.g., cyclohexyl polyether urethanes) are used as a membrane coating, where linear or cyclic aliphatic diisocyanates are used. Isocyanates of natural origin (e.g., lysine-diisocyanate) are also suitable. Cyclohexyl polyether urethanes are believed to provide good biocompatibility to the membrane and to suppress or even eliminate fouling of the membrane.

In an aspect of the invention, the hydrophilic polyurethanes comprise backbone segments of polyethylene glycol, —(CH$_2$—CH$_2$—O—)$_n$—, in an exemplary weight ratio of polyethylene glycol segments of at least about 5% (w/w), such as at least about 7% (w/w) or at least about 10% (w/w). A significant content of polyethylene glycol segments is expected to provide proper hydrophilic characteristics and to improve blood compatibility.

Suitable examples of preferred hydrophilic polyurethanes are those disclosed, e.g., in U.S. Pat. No. 5,322,063 which is hereby incorporated by reference in its entirety.

In an aspect of the invention, the hydrophilic polyurethane comprises backbone segments of polysaccharides (e.g., alginate, carrageenanes, pectin and dextranes), poly(HEMA), partly hydrolysed polyvinyl acetate (PVA) or cellulose derivatives (e.g., hydroxyethyl methyl cellulose, and carboxymethyl cellulose), in an exemplary weight ratio of the respective polysaccharide, polyvinyl acetate or cellulose derivative segments of at least about 5% (w/w), such as at least about 7% (w/w) or at least about 10% (w/w).

Examples of suitable commercially available hydrophilic polyurethanes include, but are not limited to, Hydromed D4 (water content when wetted: 50% (w/w)) and Hydromed D640 (water content when wetted: 93% (w/w)). Both polyurethanes are tradenames of Cardiotech International Inc., Wilminton, Mass., USA).

The Hydromed D4 and D640 products comprise a central polybutyleneoxide segment and polyalkyleneoxide terminal groups. The polyalkylenoxide groups may either be polyethyleneoxides or polyethyleneoxide-polypropyleneoxide-polyethyleneoxide. In both instances, the polyethyleneoxide segments are preferably longer than the length of the polybutyleneoxide and polypropyleneoxide segments. This appears to facilitate sufficient hydrophilicity and water-absorption as well as a suitable blood compatibility.

In another embodiment, the hydrophilic polymer is a hydrophilic poly(meth)acrylate.

Examples of hydrophilic poly(meth)acrylates include acrylic copolymers with first monomer units consisting of an acrylic ester having a poly(ethylene oxide) substituent as part of the alcohol moiety of the ester, and a one or more second monomer units selected from methacrylates and acrylates. The poly(ethylene oxide) substituent of the first monomer units typically has an average molecular weight of about 200 to about 2000, e.g., about 500 to about 1500. Examples of such first monomers include methoxy poly(ethylene oxide) methacrylates, methoxy poly(ethylene oxide) acrylates, etc. Examples of the second monomer units include methyl methacrylate, ethyl acrylate, butyl methacrylate, etc.

Preferred hydrophilic poly(meth)acrylates include the acrylic copolymers disclosed in WO 93/15651 A1 which is hereby incorporated by reference in its entirety.

In an exemplary embodiment, a combination of monomers is methoxy poly(ethylene oxide) methacrylates, ethyl acrylate and methyl methacrylate.

In another exemplary embodiment, other hydrophilic poly(meth)acrylates include those having segments or side chains of poly(vinyl pyrrolidone) (PVP).

In an aspect of the invention, the hydrophilicity of the hydrophilic polymer is such that the water content, when wetted, is in the range of about 5 to about 100% (w/w), or about 10 to about 95% (w/w), such as about 25 to about 95% (w/w), or about 45 to about 95% (w/w). The water content is typically a function of the type and content of hydrophilic polymers in, for example, the hydrophilic polyurethanes and hydrophilic poly(meth)acrylates, respectively, in the sense that a higher content of hydrophilic segments gives rise to a higher water-content (when wetted). Porosity may also play a role with respect to the preferred range for the water content, i.e. for membranes having small pores, an exemplary range for the water content may be about 5 to about 80% (w/w), or about 8 to about 40% (w/w), such as about 10 to about 30% (w/w). The properties of the cover membrane with respect to diffusion, diffusion rate and ability to exclude particularly large molecules are important.

Also to be considered is the ability of the cover membrane to allow the diffusion of glucose and, on the other hand, to limit the diffusion of $H_2O_2$. Thus, in one embodiment, the diffusion rate of $H_2O_2$ through the cover membrane relative to the diffusion rate of glucose through the cover membrane is in the range of about 3 to about 20, such as about 3 to about 15, or about 3 to about 10. Diffusion rate is determined as described in the "Experimentals" section. It is noted that the relative diffusion rates for the cover membrane are superior to the same of a typical, known polyurethane cover membrane.

In an exemplary embodiment, the apparent diffusion coefficient of glucose through the cover membrane is in the range of about 0.1 to about $5.0 \times 10^{-9}$, such as about 0.3 to about $1.5 \times 10^{-9}$, or such as about 0.5 to about $1.1 \times 10^{-9}$, for a glucose sensor. For a corresponding lactate sensor, the apparent diffusion coefficient of lactate through the cover membrane may be in the range of about 0.5 to about $5 \times 10^{-10}$, such as about 1.2 to about $3.2 \times 10^{-10}$. Apparent diffusion coefficients are measured as described in the "Experimentals" section.

Of further relevance is the ability of the cover membrane to exclude "large" molecules (e.g., peptides, proteins and enzymes such as the enzymes of the enzyme layer (e.g., glucose oxidase and lactate oxidase)), while at the same time allowing diffusion of the relevant analyte, e.g., lactate, glucose, creatine, creatinine, etc. Such analytes typically have a molecular weight of up to about 200 whereas peptides, proteins and enzymes may have molecular weights of from about 300 for small peptides to several thousands or more for proteins, e.g. about 30,000 for glucose oxidase.

The cover membrane layer (in wet form) may have a thickness of in the range of about 5 to about 40 µm, such as about 6 to about 30 µm, or such as about 10 to about 17 µm, for conventional sensors. For thick-film sensors, the cover membrane layer (in wet form) may have a thickness of in the range of about 1 to about 20 µm, such as about 2 to about 10 µm, or such as about 3 to about 5 µm.

The hydrophilic polymer layer of the cover membrane in dry form may also have a thickness of in the range of about 0.1 to about 5 µm, such as about 0.25 to about 3 µm, or such as about 0.5 to about 1 µm, particularly for thick-film sensors.

In an exemplary embodiment, the hydrophilic polymer layer of the cover membrane in dry form has a thickness of in the range of about 100 to about 2000%, such as about 100 to about 1000%, or such as about 200 to about 500%, of the average size of the pores of the polymeric material.

In view of the preferred water-absorption properties, the ratio between the thickness of the cover membrane in wet form and the thickness of the cover membrane in dry form may be in the range of about 2:1 to about 1:1.

In an exemplary embodiment, the ratio between the thickness of the hydrophilic polymer layer of the cover membrane in wet form and the thickness of the hydrophilic polymer layer of the cover membrane in dry form is in the range of about 100:1 to about 1:1, or about 80:1 to about 2:1.

In some embodiments, in particular for conventional sensors, the ratio between the thickness of the hydrophilic polymer layer of the cover membrane in wet form and the thickness of the hydrophilic polymer layer of the cover membrane in dry form may be in the range of about 20:1 to about 1.5:1, such as in the range of about 10:1 to about 2:1. In some other embodiments, in particular for conventional sensors, e.g., with track-etched membranes, the ratio between the thickness of the hydrophilic polymer layer of the cover membrane in wet form and the thickness of the hydrophilic polymer layer of the cover membrane in dry form is in the range of about 80:1 to about 10:1, such as in the range of about 50:1 to about 30:1.

For planar sensors, e.g., with solvent-cast membranes, the ratio between the thickness of the hydrophilic polymer layer of the cover membrane in wet form and the thickness of the hydrophilic polymer layer of the cover membrane in dry form may be in the range of about 10:1 to about 2:1, such as in the range of about 6:1 to about 3:1.

In other embodiments, the weight ratio between the at least one porous polymeric material and the hydrophilic polymer (non-wetted) is in the range of about 100:1 to about 1:1, e.g., about 80:1 to about 10:1, or about 50:1 to about 30:1.

In one embodiment of the invention, the cover membrane is the outermost layer of the enzyme sensor.

Several advantages have been identified by using, for example hydrophilic polyurethane to cover the outer surface (and pore mouths) of at least one face of the at least one porous polymeric material. For one, the polyurethane has small pores which effectively block the pores of the porous polymeric material for penetration/migration of enzymes/proteins, while still allowing for the diffusion of smaller hydrophilic and hydrophobic molecules. Further, the hydrophilic polyurethane is normally not soluble in water, although the polyurethane is swellable and is capable of holding substantial amounts of water. As a result, leaching and degeneration of the polyurethane coating will be substantially absent during the lifetime of the sensor. The same also applies, for example, to hydrophilic poly(meth)acrylates.

Electrode

The electrode of the enzyme sensor is selected with due respect to the reaction products of the analyte and the enzyme(s), e.g., an enzyme cascade as for the creatinine sensor. The electrode may be prepared from a precious metal, e.g., for example, gold, palladium, platinum, rhodium, indium or iridium, preferably gold or platinum, or mixtures hereof. Other suitable electron-conductive materials include, but are not limited to, $MnO_2$, Prussian blue, graphite, iron, nickel and stainless steel.

In some instances, it is preferred to further include additional electrodes, e.g., an internal reference electrode and/or a counter electrode, adjacent to the mandatory electrode. See, e.g., FIG. 3.

Enzyme Layer

The enzyme layer (or layers) of the enzyme sensor plays an important role in that the one or more enzymes facilitate the conversion of the analyte to a secondary species which can be detected at the electrode surface. In some embodiments, a single enzyme is used (e.g., glucose oxidase, lactate oxidase, urease), whereas a plurality of enzymes (e.g., creatinase and sarcosine oxidase) may be used to facilitate a cascade of reactions leading to a species which can be detected at the electrode.

The enzyme(s) may either be deposited as such, or in a direct or indirect immobilised form, e.g., embedded or mixed in a polymer, or cross-linked, or immobilised to an underlying layer or to the cover layer so as to reduce or eliminate migration. In some embodiments, a plurality of enzymes may be arranged in separate layers. The enzyme layer may also be held in place by a ring or gasket so as to avoid use of excessive amounts of enzyme and so as to ensure that a well-determined amount of enzyme is placed in a well-defined region of the sensor membrane.

The enzyme layer may comprise at least one enzyme including, but not limited to, carbohydrate oxidase, glucose oxidase, galactose oxidase, glycolate oxidase, aldose oxidase, pyranose oxidase, lactate oxidase, alpha-hydroxy acid oxidase, sarcosine oxidase, alcohol oxidase, glycerol oxidase, amine oxidase, amino acid oxidase, cholesterol oxidase, urease, bilirubin oxidase, laccase, peroxidase, glucose dehydrogenase, lactate dehydrogenase, glutamate dehydrogenase, P-450, superoxide dismutase, catalase, creatininase, creatinase, and related co-enzymes.

For detection of creatine, the enzyme layer in a particular embodiment comprises creatinase and sarcosine oxidase. For detection of creatinine, the enzyme layer in a particular embodiment comprises creatininase, creatinase and sarcosine oxidase. For detection of glucose, the enzyme layer in a particular embodiment comprises glucose oxidase. For detection of lactate, the enzyme layer in a particular embodiment comprises lactate oxidase. For detection of urea, the enzyme layer in a particular embodiment comprises urease.

Further Layers

In an embodiment of the invention, the enzyme layer is not in direct contact with the electrode. Thus, the enzyme sensor may comprise 1 to about 3 layers separating the electrode and the enzyme layer. Such layer(s) typically include(s) an intermediate layer, e.g., an interference limiting layer. The layer(s) may also include a water-containing porous spacer layer separating the electrode and the intermediate layer.

In one embodiment, at least one layer separating the electrode and the enzyme layer is a layer of a material including, but not limited to, cellulose acetate (CA), Nafion™, hard PVC, Baytron™, electropolymerised polymers (e.g. polythiophenes, 1,3-diaminobenzenes, phenols), and SPEES-PES (polyaryl-ethersulphone/polyethersulphone copolymer). Such a layer may function as an interference limiting layer. In one embodiment, the intermediate layer is an interference limiting cellulose acetate (CA) layer.

In another embodiment, (which may be combined with the above-described embodiment), at least one layer separating the electrode and the enzyme layer is a water-containing porous spacer layer.

When the sensor is used to detect analytes which are present in very low concentrations (e.g., creatinine, creatine or other analytes with a detection limit in the range of 1-20 µM), it has been observed that fluid samples without the analyte can cause a false signal on the electrode. The false signals may correspond to a signal from −25 µM to 25 µM analyte, and they stem from differences (other than the analyte, which is zero) in the composition of the various liquids brought into contact with the enzyme sensor, e.g., blood samples, cleaning liquids, wetting liquids, calibration liquids, etc. The observation of false signals is probably due to a combination of two factors:

First, non-ionic species diffuse more rapidly across the interference limiting layer than ionic species. Therefore, bicarbonate/$CO_2$ present in the sample but not in the rinse solution will cause the pH below the interference limiting layer to drop. The same effect is seen with imidazole/H-imidazole being present in most rinse solutions but not in the samples. A drop in pH will cause a drop in the zero current that stems from oxidation of water.

Second, the concentration of ionic species at the anode surface changes as a function of the different samples. Such changes will lead to changes in the ionic composition on the electrode, thereby leading to a current known as a non-faradaic current. The total amount of electric charge being transported as non-faradaic current will only depend on the difference in ionic composition; however, the time constant of the diffusion can be changed.

It has been found that the above problem can be alleviated by introducing a water-containing porous spacer layer between the anode and the interference limiting layer. The water in the water-containing spacer layer will buffer the changes in ionic composition experienced by the anode. Thus, the non-faradaic current will be extended over a longer time interval and therefore have a smaller amplitude. Diffusion is a very rapid process at small distances (i.e., less than about 1 s for 02 diffusion over about 50 µm). Therefore, the spacer layer functions only in combination with a diffusion resistance (i.e., the interference limiting layer), so that the system functions like a capacitor in series with a resistor. It is therefore important that the interference limiting layer is rather impermeable to ions, or else the spacer layer should be very thick.

Suitable examples of materials forming the porous polymeric matrix of the water-containing porous spacer layer for conventional sensors (track-etched or solvent-cast) are the same as described above for the porous polymeric materials. In one embodiment, the materials include, but are not limited to, polyethylene terephthalate (PETP), polyvinyl chloride, and polycarbonate. In a particular embodiment, the material of the spacer layer for such sensors is polyethylene terephthalate (PETP). Such spacer layers may be track-etched and functions as a water-containing porous spacer layer separating the electrode from the intermediate layer or the enzyme layer.

Suitable examples of materials forming the porous polymeric matrix of the water-containing porous spacer layer for planar sensors, e.g., thick-film sensors (solvent-cast), include polymers that are not limited to hydrophilic polyurethanes, hydrophilic poly-(meth)acrylates, poly(vinyl pyrrolidone), polyurethanes, Nafion™-polymers, electro-polymerised polymers (e.g., polythiophenes, 1,3-diaminobenzenes, phenols), and SPEES-PES (polyaryl-ethersulphone/polyethersulphone copolymer). Alternatively, the material forming the porous polymeric matrix may be selected from the same materials as described above for the porous polymeric materials mixed with a porosity forming compound (e.g., detergents or water-soluble hydrophilic polymers), in particular, polyvinyl chloride, and polycarbonate, mixed with such porosity forming compounds. Such a layer functions as a water-containing porous spacer layer separating the electrode from the intermediate layer or the enzyme layer.

The term "water-containing porous spacer layer" is intended to mean a layer which, when the sensor is in use, provides a buffering effect in the sense that pH instability at the electrode surface is reduced.

In the present context, the term "water-containing" used in connection with the porous spacer layer is intended to mean that the porous polymeric matrix comprises a substantial amount of water, e.g., an amount of at least about 6% based on the weight of the porous polymeric matrix. The water content may be even higher, e.g., at least about 8%, at least about 10%, at least about 20%, at least about 25%, at least about 40% or at least about 50% or higher. For solvent-cast planar sensors, the total degree of swelling (water-uptake) is a consideration, because an excessive water-uptake may be detrimental to the structural integrity of the enzyme membrane. Thus, in a particular embodiment for planar sensors, the water content does not exceed about 200%, such as about 150%.

It should be understood that the optional spacer layer of the enzyme sensor is generally described in its ready-to-use form, i.e., the form where the water-containing porous spacer layer contains a substantial amount of water, and wherein the enzyme sensor is capable of measuring an analyte in a fluid sample. In one embodiment, the enzyme sensor is stored and delivered to the end-user in dry form, i.e., in a form where the spacer layer is substantially dry. Thus, the end-user will have to wet the membrane of the enzyme sensor with an aqueous liquid such that the spacer layer, which is capable of absorbing a substantial amount of water, converts into a water-containing porous spacer layer. Other layers (e.g., the cover membrane) may also be able to absorb a substantial amount of water.

In respect to a conventional enzyme sensor construction, the wetting may be conducted by means of the internal liquid of the enzyme sensor. See, e.g., FIG. 1. Planar sensors are typically wetted by specific wetting liquids, cleaning liquids or calibration liquids, etc.

It is believed to be advantageous to include a buffer, a cation-exchange material or an electrolyte salt in the spacer layer to further limit the effect of bicarbonate ($HCO_3-$) in the fluid samples and other liquids. Thus, in one embodiment, the water-containing porous spacer layer further comprises one or more components selected from, for example, buffers, electrolyte salts (e.g., electrolyte polymers) and cation-exchange materials.

The spacer layer may have a porosity in the range of about 0.0005 to about 2% (vol/vol) for track-etched materials and in the range of about 1 to about 90% for solvent-cast materials.

For conventional creatinine/creatine and urea sensors with a track-etched spacer layer, the porosity may be in the range of about 0.05 to about 0.1%, such as about 0.2 to about 0.25%. For conventional lactate sensors with a track-etched spacer layer, the porosity may be in the range of about 0.0005 to about 0.015%, such as about 0.003 to about 0.004%. For conventional glucose sensors with a track-etched spacer layer, the porosity may be in the range of about 0.001 to about 0.05%, such as about 0.01 to about 0.02%. The porosity for track-etched membranes is determined as: porosity (%)=$\pi \times$ (pore diameter/2)$^2 \times$(pore density)$\times 100\%$. The average pore size of the spacer layer may be in the range of about 0.05 to about 250 nm, such as about 1 to about 150 nm, or such as about 10 to about 110 nm, and the pore density may be the range of about 40,000 to about 40,000,000 pores per $cm^2$.

The porosity for solvent-cast spacer layers may most easily be determined as the volume occupied by water when the membrane is wetted with water. The porosity of solvent-cast spacer layers may be in the range of about 1 to about 90%, such as about 3 to about 85%. The difference of at least one order of magnitude between the porosity of track-etched membranes and solvent-cast membranes can be explained by the fact that only the "effective" pores of the track-etched membranes are taken into account, whereas all pores and cavities are included in the determination of porosity for the solvent-cast membranes.

The water-containing porous spacer layer may have a thickness in the range of about 0.2 to about 20 μm, such as about 0.5 to about 15 μm. For planar sensors, the thickness may be in the range of about 0.2 to about 10 μm, such as about 0.5 to about 5 μm. For conventional sensors, the thickness may be in the range of about 1 to about 20 μm, such as about 2 to about 15 μm.

The water-containing porous spacer layer may be in the form of a solvent-cast layer or in the form of a track-etched membrane. In an aspect of the invention, the spacer layers for planar sensors, e.g., thick-film sensors, are formed by the mixing of the above-described polymeric materials with a porosity forming compound (e.g., a detergent, water-soluble hydrophilic polymer, etc.) to obtain a suitable porosity.

In the case of conventional sensors, track-etched membranes are preferred because it is believed to be important that the pores are oriented substantially perpendicular relative to the electrode surface (see e.g., FIG. 1) such that the secondary species to be detected at the electrode is directed more accurately to the electrode surface.

The sensor may be of the conventional type and the water-containing porous spacer layer may be a track-etched polyethylene terephthalate material. Alternatively, the sensor may be of the planar type and the water-containing porous spacer layer may be a solvent-cast layer of, for example, hydrophilic polyurethane or hydrophilic poly(meth)acrylate, preferably mixed with a porosity forming compound, e.g., a detergent, a water-soluble hydrophilic polymer, etc.

The water-containing porous spacer layer and the intermediate layer may be combined into a heterogeneous layer of materials of the type described for the intermediate layer and the spacer layer. The layer is formed in such a manner that the material of the spacer layer is dispersed in a continuous phase of the material of the intermediate layer.

For the various embodiments defined above, it is preferred that the 1-3 layers separating the electrode and the enzyme layer is capable of limiting the diffusion of chemical compounds such as paracetamol, ascorbic acid and uric acid in such a manner that the signal is reduced by at least about 90%, such as at least about 95%, for an initial period of 15 seconds.

An exemplary embodiment of the invention relates to an enzyme sensor for determining the concentration of creatine in a fluid sample, said sensor comprising a metal electrode (e.g., a platinum electrode), a water-containing porous spacer layer (e.g., of polyethylene terephthalate (PETP)), in contact with said metal electrode, an interference limiting layer (e.g., of a cellulose acetate (CA)) in contact with said spacer layer, an enzyme layer comprising sarcosine oxidase and creatinase in contact with said cellulose acetate layer, and a cover membrane layer for said enzyme layer, wherein said cover membrane layer comprises a porous polyethylene terephthalate material, and wherein the outer surface and pore mouths of at least one face of the at least one porous polymeric material are covered by, for example, a hydrophilic polyurethane comprising backbone segments of polyethylene glycol in a weight ratio of polyethylene glycol segments of at least about 5% (w/w) and/or have a water content when wetted of at least about 25% (w/w). Preferably, the porous polymeric material of the cover membrane layer is at least partly impregnated with the hydrophilic polyurethane.

Another exemplary embodiment of the invention relates to an enzyme sensor for determining the concentration of creatinine in a fluid sample, said sensor comprising a metal electrode (e.g., platinum electrode), a water-containing porous spacer layer (e.g., of polyethylene terephthalate (PETP)) in contact with said metal electrode, an interference limiting layer (e.g., of a cellulose acetate (CA)) in contact with said spacer layer, an enzyme layer comprising e.g., sarcosine oxidase, creatininase and creatinase in contact with said interference limiting layer, and a cover membrane layer for said enzyme layer, wherein said cover membrane layer comprises, for example, a porous polyethylene terephthalate material, and wherein the outer surface and pore mouths of at least one face of the at least one porous polymeric material are covered by, for example, a hydrophilic polyurethane comprising backbone segments of polyethylene glycol in a weight ratio of polyethylene glycol segments of at least about 5% (w/w) and/or have a water content when wetted of at least about 25% (w/w). Preferably, the porous polymeric material of the cover membrane layer is at least partly impregnated with the, for example, hydrophilic polyurethane.

Another exemplary embodiment of the invention relates to an enzyme sensor for determining the concentration of lactate in a fluid sample, said sensor comprising a metal electrode (e.g., a platinum electrode), an interference limiting layer (e.g., of a cellulose acetate (CA)) in contact with said metal electrode, an enzyme layer comprising, for example, lactate oxidase in contact with said interference limiting layer, and a cover membrane layer for said enzyme layer, wherein said cover membrane layer comprises, for example, a porous polyethylene terephthalate material, and wherein the outer surface and pore mouths of at least one face of the at least one porous polymeric material are covered by, for example, a hydrophilic polyurethane comprising backbone segments of polyethylene glycol in a weight ratio of polyethylene glycol segments of at least about 5% (w/w) and/or have a water content when wetted of at least about 25% (w/w). Preferably, the porous polymeric material of the cover membrane layer is at least partly impregnated with the, for example, hydrophilic polyurethane.

Another exemplary embodiment of the invention relates to an enzyme sensor for determining the concentration of glucose in a fluid sample, said sensor comprising a metal electrode (e.g., a platinum electrode), an interference limiting layer (e.g., of a cellulose acetate (CA)) in contact with said metal electrode, an enzyme layer comprising glucose oxidase in contact with said interference limiting layer, and a cover membrane layer for said enzyme layer, wherein said cover membrane layer comprises, for example, a porous polyethylene terephthalate material, and wherein the outer surface and pore mouths of at least one face of the at least one porous polymeric material are covered by a, for example, hydrophilic polyurethane comprising backbone segments of polyethylene glycol in a weight ratio of polyethylene glycol segments of at least about 5% (w/w) and/or have a water content when wetted of at least about 25% (w/w). Preferably, the porous polymeric material of the cover membrane layer is at least partly impregnated with the, for example, hydrophilic polyurethane.

Cover Membranes

An aspect of the present invention relates to a membrane of a track-etched material, at least partly impregnated with a hydrophilic polymer. Exemplary hydrophilic polymers include hydrophilic polyurethanes and hydrophilic poly(meth)acrylates, in particular a hydrophilic polyurethane.

Another aspect of the present invention relates to a membrane of a porous polyethylene terephthalate material at least partly impregnated with a hydrophilic polymer. Exemplary hydrophilic polymers include hydrophilic polyurethanes and hydrophilic poly(meth)acrylates, in particular a hydrophilic polyurethane. The material is preferably track-etched. Also, the exemplary polyethylene terephthalate material may have a porosity of in the range of about 0.003 to about 2%.

Another aspect of the present invention further relates to a solvent-cast membrane of, for example, a polyvinyl chloride material at least partly impregnated with a hydrophilic polymer. Exemplary hydrophilic polymers include hydrophilic polyurethanes and hydrophilic poly(meth)acrylates, in particular a hydrophilic polyurethane. The exemplary polyvinyl chloride material may have a porosity of in the range of in the range of about 2 to about 30%.

The above-described specifications for the exemplary cover membranes also apply to the above-defined cover membranes, mutatis mutandis.

Use of Enzyme Sensors

The enzyme sensors of the invention may be exposed to a wetting or calibration fluid before its first use, normally until the signal is stabilized.

Measurements of, e.g., creatinine, creatine, glucose, lactate, etc. in samples of physiological fluids may take place in various automated or semi-automated analysers, many of which employ multiple sensors to measure multiple parameters. One example is a clinical analyser, particularly a blood analyser. The fluid sample is introduced manually or automatically into a flow system of the analyser or into a flow system of a cassette for introduction into the analyser. Sensors for one or more parameters of the physiological sample may thus be exposed to the fluid sample introduced into the flow system.

Hence, the present invention also provides an apparatus for determining the concentration of an analyte in a fluid sample, said apparatus comprising one or more enzyme sensors as defined herein.

Furthermore, the present invention also provides a method of determining the concentration of an analyte in a fluid sample, said method comprising the steps of contacting the fluid sample with an enzyme sensor as described herein, and conducting at least one measurement involving the electrode of the enzyme sensor.

The sensors are normally exposed to the fluid sample and other fluids, e.g., wetting fluids, cleaning fluids, calibration fluids, etc. that are conducted to and from the sensor.

Method of Cleaning an Enzyme Sensor

It has surprisingly been found that the principles behind the present invention render it possible to utilize proteases in cleaning liquids for enzyme sensors. Thus, the present invention also relates to a method of cleaning an enzyme sensor, said sensor comprising an electrode, at least one enzyme layer and a cover membrane layer for at least one enzyme layer, the method comprising the step of contacting the surface of the cover membrane to a cleaning solution comprising a protease.

An example of a suitable protease for cleaning the cover membrane of enzyme sensors is Subtilisin A.

It should be understood that the cleaning step is preceded and followed (but not necessarily immediately preceded and followed) by measuring steps, where a fluid sample is measured. Thus, the method may further comprise steps of measuring the concentration of an analyte before, as well as after, the step of contacting the cover membrane with the cleaning solution.

In an exemplary embodiment, the cover membrane comprises at least one porous polymeric material, wherein the outer surface and pore mouths of at least one face of the at least one porous polymeric material are covered by a hydrophilic polymer. Exemplary hydrophilic polymers include hydrophilic polyurethanes and hydrophilic poly(meth)acrylates.

The above description is not intended to limit the claimed invention in any manner. Furthermore, the discussed combination of features might not be absolutely necessary for the inventive solution. In addition, the disclosures of all publications, patents or published applications cited herein are incorporated by reference in their entireties.

The present invention will be further illustrated in the following examples. However, it is to be understood that these examples are for illustrative purposes only, and should not be used to limit the scope of the present invention in any manner.

EXPERIMENTALS

Materials

Creatininase from *Pseudomonas putida* was obtained from Roche Diagnostics, Mannheim, Germany. Hydromed D4, Hydromed D640 and Hydromed TP were obtained from Cardiotech International Inc., Wilminton, Mass., USA General Procedure Measurement of Diffusion Properties The diffusion properties can be determined in a diffusion cell, where a value for the apparent diffusion coefficient for a substrate is obtained as the result of the total porosity and the diffusion coefficient of the substrate in water. "Apparent diffusion coefficient" means the "efficient" diffusion coefficient for the entire membrane area not taking into account the porosity of the membrane.

The diffusion cell (diameter 15 mm, having an O-ring) should be absolutely clean before use. In order to reduce contamination, it is advisable to have the solution with the high substrate concentration in the cell half where the O-ring is arranged. The fluid sample for analysis is loaded into the cell half without the O-ring. A membrane sample approximately ½ cm larger than the opening between the cell halves is cut and is arranged on top of the O-ring. The cell is then closed and tightened. The diffusion cell with the membrane and a magnetic bar (10 mm) is placed on a magnetic stirrer (320±30 r.p.m.). Approximately 30 mL of a substrate solution in cleaning liquid (S4970) and 30 mL of pure cleaning liquid (S4970) are simultaneously loaded into the two half cells of the diffusion cell. After 48 and 72 hours, respectively, the substrate concentration in the pure cleaning liquid is measured by taking out a 1 mL sample with a syringe and filling up with 1 mL of the pure cleaning liquid. The substrate concentration in the samples is measured on an ABL™ 735 Blood Gas Analyzer (Radiometer Medical ApS, Copenhagen, Denmark).

The apparent diffusion coefficient is determined as follows. The flux: in all systems, a passive transport process of a compound will take place if the distribution of the compound in the system does not correspond to the thermodynamic equilibrium distribution of the compound. The flux is defined as the amount of compound which passes through an area unit (area perpendicular to the direction of the transport) per second, and has the unit J=amount·cm$^{-2}$·s$^{-1}$.

Fick's 1st law is valid for a stationary diffusion, i.e., a linear concentration gradient has been established.

$$J = -D\frac{dC}{dx}$$

where D is the diffusion coefficient for the compound, i.e., a value characteristic for the diffusing molecule type under the given conditions (It does not only include the factors determining the rate of transport, such as size and form, but also properties of the surrounding medium like, e.g., viscosity); dC/dx is the slope of the concentration profile at point x (the value dC/dx is also referred to as the concentration gradient in direction x, where the sign character shows the direction in which the concentration increases, i.e., a positive value for dC/dx shows that the concentration increases in the positive direction of the x-axis).

Determination of Apparent Diffusion Coefficient For Analytes Over Coated Cover Membranes A porous membrane of an approximately 12 µm layer of polyethyleneetherephthalate (PETP) (pore diameter approximately 0.1 µm; pore density: $1.6 \cdot 10^6$ pores/cm$^2$) was impregnated with a hydrophilic polyurethane (PUR; Hydromed D4 and/or Hydromed D640) by fully immersing sheets of a size of 150·200 mm in a 1% solution of PUR in 96% EtOH. After 5 seconds, the membrane was removed from the solution at a constant speed of around 50 mm/s. Afterwards, the membrane was allowed to dry until the ethanol had evaporated (less than 30 minutes). The sheets were subsequently cut into suitable pieces, where necessary.

Figure 6:
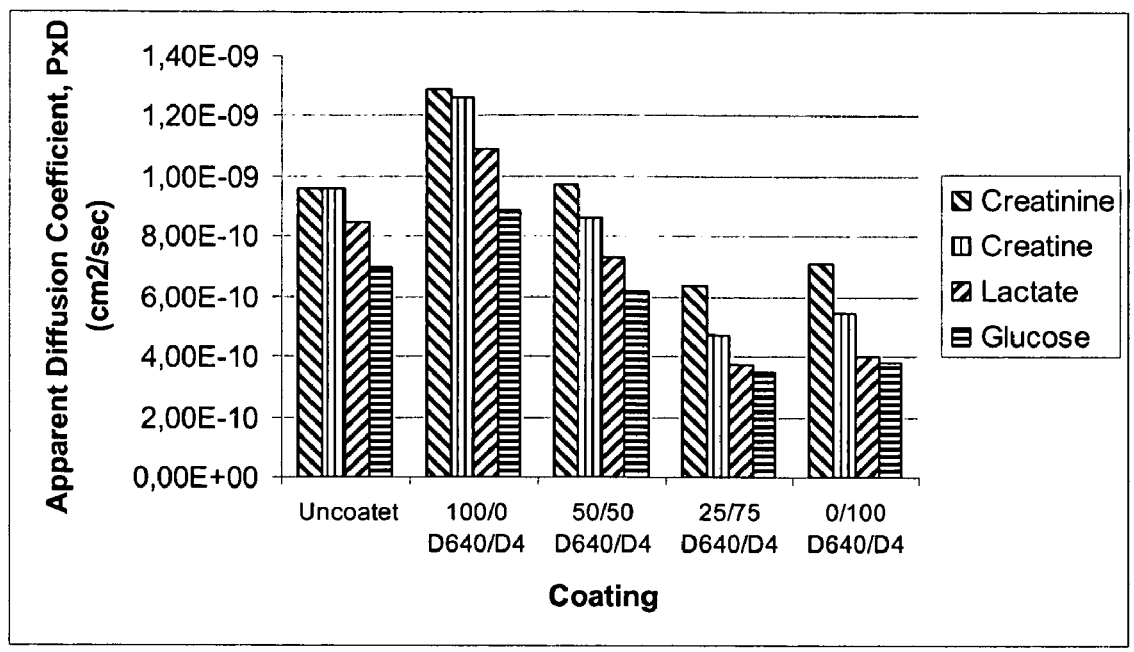
FIG. 6 shows that it is possible to modify the diffusion coefficient of a track-etched membrane by altering the composition of the hydrophilic polyurethane coating using the same porous polymeric material.

The membranes were arranged in a diffusion cell (see above) in order to determine the apparent diffusion coefficient (cm$^2$/s) for various analytes. The results are shown in FIG. 6. The results show that it is possible to control the diffusion coefficient of a PETP membrane by altering the composition of the hydrophilic polyurethane coating.

General Sensor Construction (Conventional Sensor Type)

Figure 1:
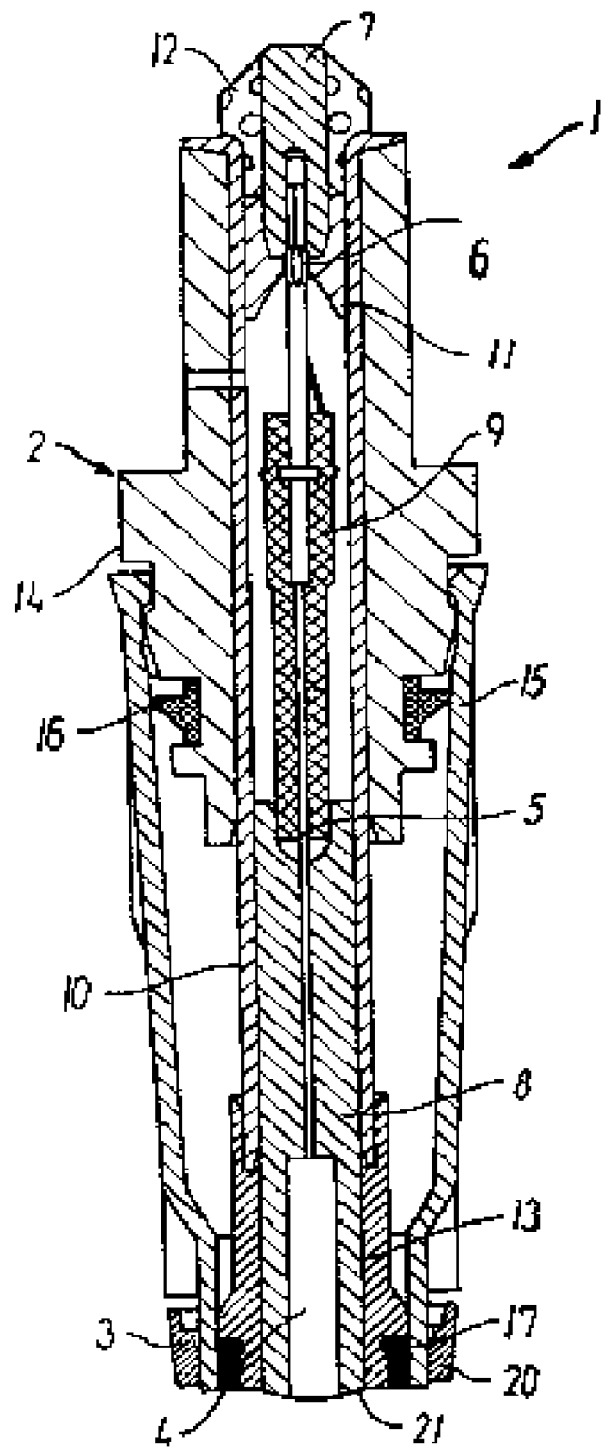
FIG. 1 illustrates a conventional enzyme sensor comprising an electrode and a membrane.

With reference to FIG. 1, the sensor 1 comprises an electrode 2 onto which a membrane ring 3 is attached. The electrode 2 comprises a platinum anode 4 connected with a platinum wire 5 which, through a micro plug 6, is connected with a silver anode contact body 7. The platinum anode 4 and the lower part of the platinum wire 5 are sealed into a glass body 8. Between the glass body 8 and the micro plug 6, the platinum wire 5 is protected with a heat shrink tubing. A tubular silver reference electrode 10 encircles the upper part of the glass body 8 and extends in the length of the electrode 2 to the anode contact body 7 which is fastened inside the reference electrode by means of a fixing body 11 and epoxy 12. The lower part of the glass body 8 is surrounded by an electrode base 13 whereto the membrane ring 3 is attached.

Figure 2:
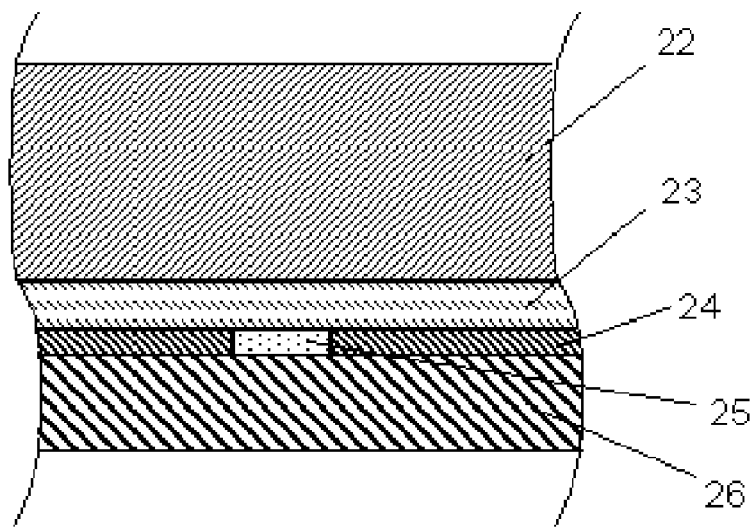
FIG. 2 illustrates the membrane of the sensor of FIG. 1.

With reference to FIGS. 1 and 2, the upper part of the reference electrode 10 is surrounded by a plug part 14 for mounting the electrode 2 in the corresponding plug of an analysis apparatus (not shown) and for fixing a mantle 15. Gaskets 16 and 17 are placed between the electrode 2 and the mantle 15 in order to ensure that any electrolyte located at the measuring surface of the electrode 2 does not evaporate. The membrane ring 3, which is mounted at one end of the mantle 15, comprises a ring 20. A membrane 21 is stretched over the lower opening of the ring 20. This membrane 21 is shown in detail in FIG. 2 and as described in detail in Examples 2 and 3.

General Sensor Construction (Thick-Film Sensor Type)

FIG. 3 illustrates an exemplary planar, thick-film sensor construction formed on a dielectric substrate (110) where a working electrode (120) and a reference electrode (130;140) are formed. The electrodes are bordered by a two-layer dielectric encapsulant (150;160 and 151;161). The working electrode is covered by a water-containing porous spacer layer (121), an intermediate layer (170), an enzyme layer (180), and a cover membrane (190) as disclosed herein.

Referring to FIG. 3, an alumina substrate 110 of a thickness of 200 µm is provided at one surface with a circular platinum working electrode 120 of a diameter 1000 µm and a thickness of 10 µm, an annular platinum counter electrode 130 of an outer diameter 3000 µm, an inner diameter 2000 µm and a thickness of 10 µm, covering the angular range 30-330° of the outer periphery of the working electrode, and a circular silver/silver chloride reference electrode 140 of a diameter 50 µm, positioned at the outer periphery of the working electrode at 0°. All of these three electrode structures are connected to the sensor electronics (not shown) across the alumina substrate 110 via platinum filed through holes (not shown) traversing the substrate. Upon operation, the working electrode 120 is polarised to +675 mV vs. the reference electrode 140.

Further on the alumina substrate 110 are two-layered structures of glass and polymer encapsulant. These two-layered structures include an annular structure 160, 161 of an outer diameter 1800 µm, an inner diameter 1200 µm and a thickness of 50 µm surrounding the working electrode 120 and a structure 150, 151 of a thickness 50 µm surrounding the complete electrode system. Both of these two-layered structures consist of an inner layer 150, 160 facing the alumina substrate 110 of ESL glass 4904 from ESL Europe of the United Kingdom of a thickness of 20 µm, and an outer layer 151, 161 of polymer encapsulant from SenDx Medical Inc. of California, USA as disclosed in international patent application WO97/43634 to SenDx Medical Inc. of California, USA which comprises 28.1% by weight of polyethylmethacrylate (Elvacite, part number 2041, from DuPont), 36.4% by weight of carbitol acetate, 34.3% by weight of silaninized kaolin (part number HF900 from Engelhard), 0.2% by weight of fumed silica and 1.0% by weight of trimethoxysilane.

A circular inner membrane 170 of cellulose acetate and cellulose acetate butyrate of a diameter 1200 μm and a thickness of 10 μm covers the working electrode 120.

A circular enzyme layer 180 of glucose oxidase crosslinked by glutaric aldehyde of a diameter 1200 μm and a thickness of 2 μm covers the inner membrane 170.

The enzyme layer 180 was prepared by dispensing 0.4 μl of a buffered solution of glucose oxidase crosslinked by glutaric aldehyde on the cellulose acetate membrane 170. The enzyme layer was dried 30 min. at 37° C.

A circular cover membrane layer 190 of PVC/trimethyl-nonyl-triethylene glycol/diethylene glycol of a diameter 4000 μm and a thickness of 10 μm covers the complete electrode system, centered onto the working electrode 120.

The cover membrane was prepared from 1.35 gram of poly vinyl chloride (Aldrich 34,676-4), 0.0149 gram of trimethyl-nonyl-triethylene glycol (Tergitol TMN3 from Th. Goldschmidt) and 0.134 gram diethylene glycol which were added to 21.3 gram of tetrahydrofurane and 7.58 gram of cyclohexanone. The mixture was stirred until the PVC was dissolved and a homogenous solution was obtained. 28.5 gram of tetrahydrofurane was added to obtain a 2% solution of a 90/1/9 PVC/surfactant/hydrophilic compound composition. The solution was dispensed on the sensor area to cover all three electrodes and to have an approximately 0.5 mm overlap with the polymer encapsulant 151. The cover membranes were dried for 30 min. at 23±2° C. and for 1½ hour at 40° C.

Approximately 0.3 μL of a 5% solution of a hydrophilic polyurethane (Hydromed D640/Hydromed D4 mixture having a water content of 80%) (see Example 1) in 96% EtOH was dispensed onto the dried outer membrane.

All three layers 170, 180, 190 were dispensed on an x, y, z-table mounted with an automatic dispensing unit (IVEK pump).

Example 1

Preparation of Cover Membrane for Conventional Glucose Sensor

A diffusion limiting porous membrane of an approximately 12 μm layer of polyethylene-therephthalate (PETP) (pore diameter approximately 0.1 μm; pore density: $1.6 \cdot 10^6$ pores/cm$^2$) was impregnated with a hydrophilic polyurethane (Hydromed D4) by fully immersing sheets of a size of 150*200 mm in a 1% solution of PUR in 96% EtOH. After 5 seconds, the membrane was removed from the solution at a constant speed of around 50 mm/s. Afterwards, the membrane was allowed to dry until the ethanol had evaporated (less than 30 minutes). The sheets were subsequently cut into suitable pieces, where necessary.

Example 2

Exemplary Creatine and Creatinine Sensor Constructions

Each of the creatine and the creatinine sensor are built up as known amperometric sensors. FIG. 1 shows such a sensor 1 (described above) which is suited for mounting in an apparatus for measuring the concentration of analytes in a biological sample, e.g., an ABL™ 735 Blood Gas Analyzer (Radiometer Medical ApS, Copenhagen, Denmark).

FIG. 2 shows details of the membrane 21 comprising four layers: water-containing porous spacer layer 22 facing the platinum anode 4 of the electrode 2, an interference limiting membrane layer 23, a gasket 24 encircling an enzyme layer 25, and a diffusion limiting porous polymeric material 26 which has been impregnated with a hydrophilic polyurethane having a water content of around 80%. The coated membrane layer 26 faces the sample to be analysed.

The spacer layer 22 may be a 21±2 μm track-edged membrane of polyethylene terephthalate (PETP) (pore diameter approximately 1.3-1.5 μm; pore density: $2.2 \cdot 10^7$ pores/cm$^2$). The interference limiting membrane layer 23 may be a 6±2 μm porous membrane of cellulose acetate (CA).

The gasket 24 may be a 30±5 μm double-sided adhesive disc having a center hole with a diameter of 1500 μm. The adhesive of the gasket 24 adheres to the interference limiting layer 23 and the diffusion limiting layer 26 to an extent that the enzymes are prevented from leaking out between the layers.

The enzyme layer 25 of the creatine sensor is typically an approximately 20 μm layer of creatinase and sarcosine oxidase crosslinked to glutaraldehyde mixed with suitable additives, such as buffer. The enzyme layer 25 of the creatinine sensor is typically an approximately 20 μm layer of creatininase, creatinase and sarcosine oxidase crosslinked to glutaraldehyde mixed with suitable additives, such as buffer.

The diffusion limiting porous polymeric material 26 may be an approximately 12 μm layer of polyethylenetherephthalate (PETP) (pore diameter approximately 0.1 μm; pore density: $3 \cdot 10^7$ pores/cm$^2$) which has been impregnated with a hydrophilic polyurethane (Hydromed D640/Hydromed D4 mixture having a water content of 80%) (see Example 1).

In the creatinine sensor both creatine and creatinine are converted into hydrogen peroxide. In the creatine sensor only creatine is converted into hydrogen peroxide.

At the amperometric electrode, hydrogen peroxide is oxidized anodically at +675 mV against Ag/AgCl. The resulting current flow is proportional to the creatinine/creatine concentration in the sample.

The concentration of creatinine is determined from the difference between the creatinine sensor signal (representing creatine+creatinine) and the creatine sensor signal (representing creatine).

Example 3

Exemplary Lactate Sensor Construction

Enzyme catalysed reaction between lactate and oxygen yields hydrogen peroxide ($H_2O_2$) and pyruvate. Hydrogen peroxide is then detected by an amperometric electrode. The sensor 1 (FIG. 1) is suited for mounting in an apparatus for measuring the concentration of analytes in a biological sample, e.g., an ABL™ 735 Blood Gas System (Radiometer Medical A/S, Copenhagen, Denmark).

With reference to FIG. 2 where layer 22 is omitted, the membrane 21 of the lactate sensor comprises three layers: an interference limiting membrane layer 23 facing the platinum anode 4 of the electrode 2, an enzyme layer 25, and a diffusion limiting porous membrane layer 26 facing the fluid sample. The interference limiting membrane layer 23 may be a 6±2 μm porous membrane of cellulose acetate (CA). The enzyme layer is typically an approximately 1-2 μm layer of crosslinked lactate oxidase (7 units/membrane). The diffusion limiting porous membrane layer 26 may be an approximately 12 μm layer of polyethylenetherephthalate (PETP) (pore diameter approximately 0.1 μm; pore density: $8 \cdot 10^5$ pores/ cm²) impregnated with a hydrophilic polyurethane (Hydromed D4) as described in Example 1.

Example 4

Results for the Lactate Sensor of Example 3

Linearity

Figure 9:
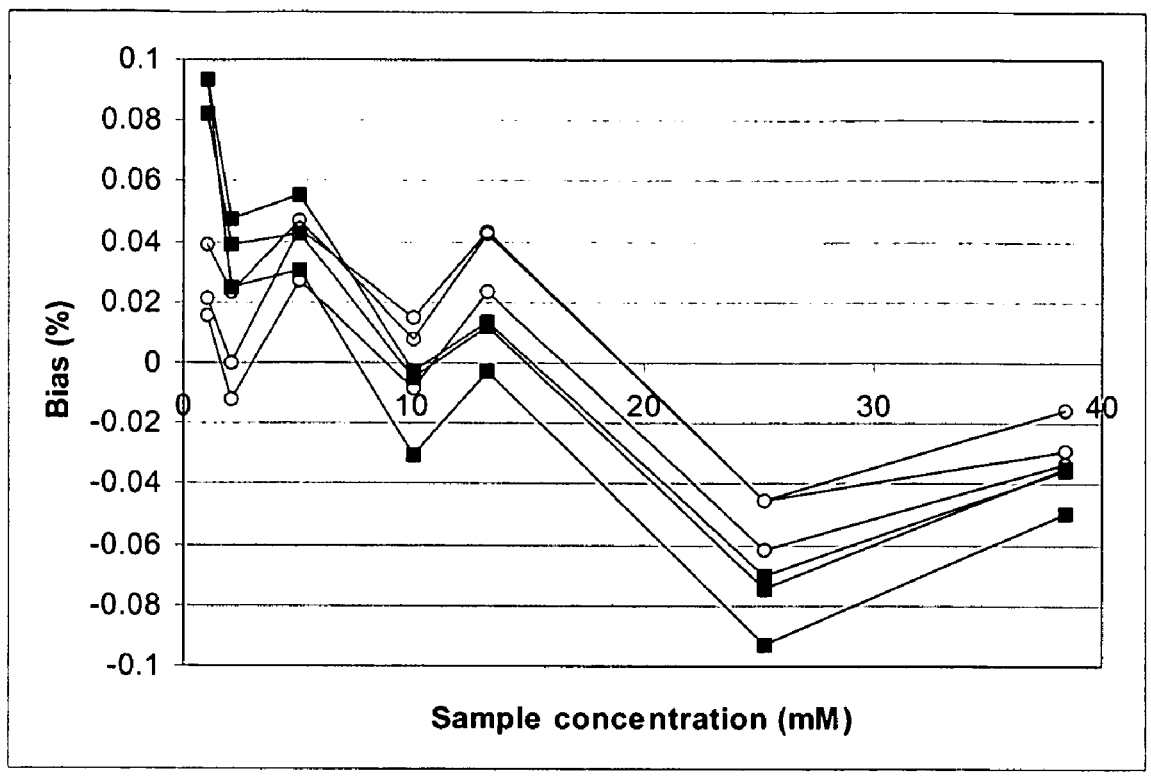
FIG. 9 illustrates the deviation of measurements on blood from true sample concentration (blood bias) for lactate sensors. Sensors without a coating are plotted using black squares and sensors with a coating are plotted using unfilled circles.

Sensors with and without the coating of the hydrophilic polyurethane are placed in an ABL735 and are calibrated regularly (once every ½-4 hours). At day 1 after mounting the sensors are exposed to different concentrations of analyte in a suitable liquid (Radiometer Rinse solution S4970). The deviation between the calculated concentration and the true concentration is plotted against the true concentration in FIG. 9. Filled squares represent sensor with uncoated membranes and open circled represent sensors with coated membranes. As can be seen, a higher deviation is observed for sensors with uncoated membranes compared to sensors with coated membranes.

Lifetime

Sensors with and without the coating of the hydrophilic polyurethane are placed in an ABL735 and are calibrated regularly (once every ½-4 hours). Once a day the sensors are quality controlled by measuring on Radiometer QC5 ampoules. The sensor lifetime is designated as the time till the sensor is not able to perform within the QC limits.

Sensitivity

Figure 7:
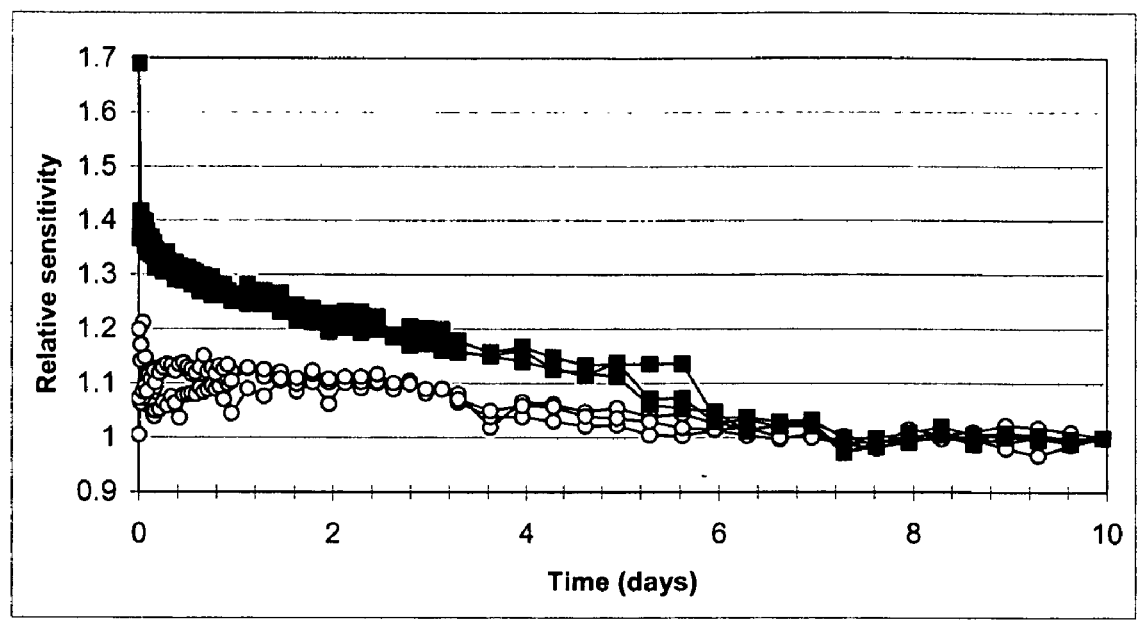
FIG. 7 illustrates the sensitivity over time for lactate sensors. The relative sensitivity (i.e., the measured sensitivity relative to the measured "steady-state" sensitivity obtained after 2-6 days (sensor type dependent)) is plotted against the time since start-up. Sensors without a coating are plotted using black squares and sensors with a coating are plotted using unfilled circles.
Figure 8:
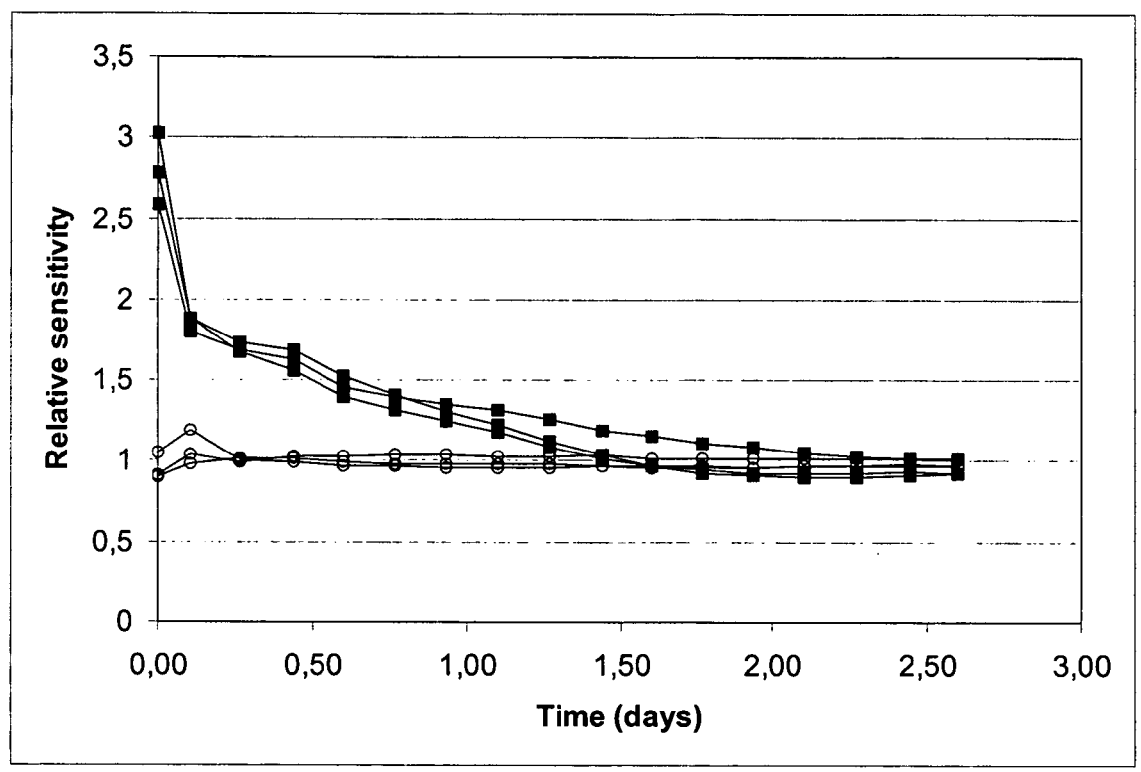
FIG. 8 illustrates the sensitivity over time for creatinine sensors. The relative sensitivity is plotted against the time since start-up. Sensors without a coating are plotted using black squares and sensors with a coating are plotted using unfilled circles.

Sensors with and without the coating of the hydrophilic polyurethane are placed in an ABL735 and are calibrated regularly (once every ½-4 hours). The measured sensitivity relative to the "steady state" sensitivity obtained after 2-6 days (sensor type dependent) is plotted against the time since start-up, see FIG. 7 for the lactate sensor (Example 3) and FIG. 8 for the creatinine sensor (Example 2).

Blood Bias/Blood Drift

Sensors with and without the coating of the hydrophilic polyurethane are placed in an ABL735 and are calibrated regularly (once every ½-4 hours). At day 1 after mounting the sensors are exposed to the same concentration of analyte in a suitable liquid (Radiometer QC5 level3) with and without added BSA (50 g/L) (BSA is added to the QC liquid in order to mimic a blood sample). Blood bias may cause the sensor to measure the same or a lower concentration in samples with protein than samples without protein.

Example 5

Reduction of Signal Over a Series of Samples

The purpose of this study was to demonstrate that a membrane coated with a hydrophilic polymer (here a hydrophilic polyurethane) used in connection with a planar sensor (here a glucose sensor—see "General sensor construction (thick-film type sensor)") renders it possible to obtain a decrease in signal for a series of sample measurements of less than 0.5% per measurement.

All sensors underwent a series of 20 consecutive blood measurements, without intermediate calibration or cleaning, with 10 mM glucose.

Results

Blood Measurement

Figure 10:
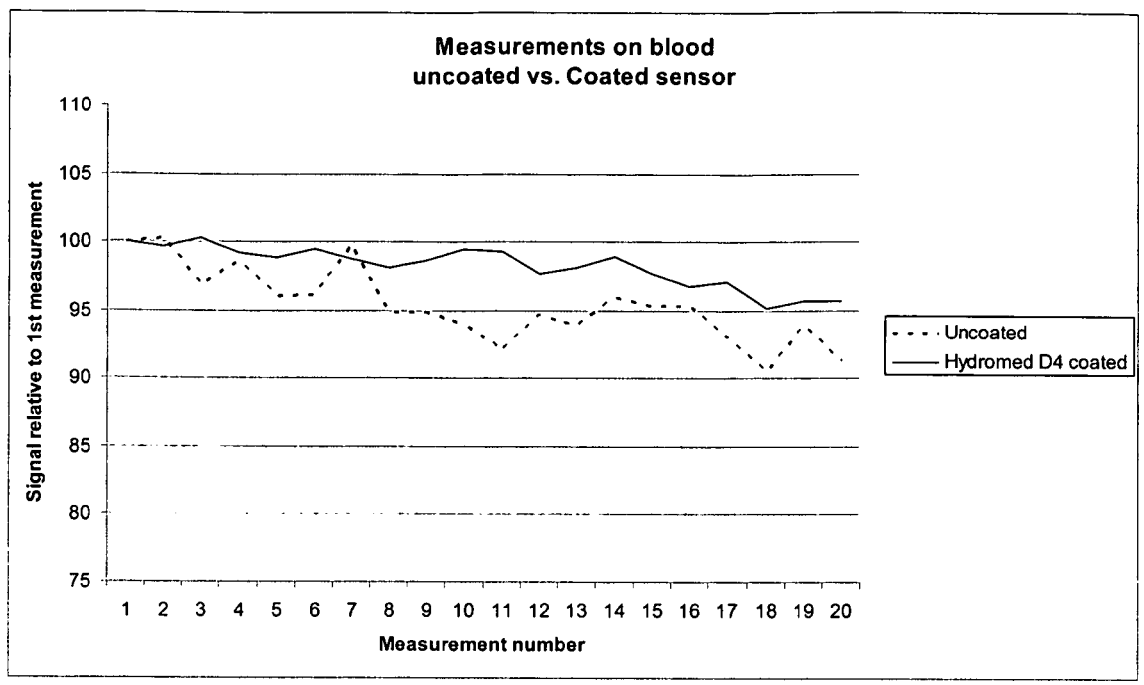
FIG. 10 illustrates the reduction of signal (blood drift) in a glucose sensor for a series of blood measurements using a planar sensor.

FIG. 10 illustrates the measured values relative to a first measurement with blood (=100) for 20 consecutive samples. The average for each of the two measurements is shown for coated (solid line) and uncoated sensors (dashed line), respectively.

It appears that a marked improvement is obtained by coating with Hydromed D4 (solid line). The decrease in the course of the series is only half of that of the series for the uncoated sensors (dashed line).

Conclusion

It was found that sensors having cover membranes coated with a hydrophilic polyurethane (Hydromed D4 from Cardiotech Inc.) result in a significantly lower decrease of signal than for corresponding uncoated sensors. The decrease in the measured values over 10 blood measurements with 10 mM glucose was approximately 2% for coated sensors whereas the decrease for corresponding uncoated sensors was approximately 6%.

This effect is related to blood drift which will cause the electrode to measure differently (lower) due to blood components (in particular, proteins and lipids) precipitating on the inner surface of the pores.

Example 6

Cleaning of Glucose Sensors With Solution Comprising Protease

In this experiment, glucose sensors (prepared as described in Example 1—two uncoated ("Without PUR") and three coated ("With PUR")) (High met. level 1 (S7570) Radiometer Medical Aps; a QC level 1 liquid) were calibrated before measurement no. 1 and no. 7 and cleaned with a Cleaning liquid (S4706 Radiometer Medical Aps) before each of measurements 2-6 and 8-12. This cleaning solution contains a protease (Subtilisin A). It can be seen from Table A that the sensitivity increases for units without a coating of hydrophilic polyurethane (PUR). Thus, the results show that it is possible to utilize a cleaning solution comprising a protease without loss of sensitivity when the cover membrane is covered with a hydrophilic polymer.

TABLE A

| Measurement No. | Without PUR | Without PUR | With PUR | With PUR | With PUR |
|---|---|---|---|---|---|
| 1 | 26.7 | 26.7 | 26.0 | 26.7 | 26.4 |
| 2 | 30.0 | 30.1 | 25.9 | 26.7 | 26.4 |
| 3 | 29.5 | 29.7 | 25.4 | 26.5 | 25.8 |
| 4 | 30.0 | 30.5 | 25.5 | 26.9 | 26.1 |
| 5 | 29.8 | 30.0 | 25.7 | 26.8 | 25.9 |
| 6 | 30.8 | 31.0 | 25.7 | 26.5 | 26.1 |
| 7 | 27.0 | 26.6 | 25.5 | 26.3 | 26.0 |
| 8 | 26.4 | 27.8 | 25.1 | 25.9 | 25.6 |
| 9 | 26.7 | 27.3 | 25.1 | 26.0 | 25.6 |
| 10 | 27.2 | 28.5 | 24.9 | 26.3 | 25.9 |
| 11 | 27.2 | 29.6 | 25.3 | 26.3 | 25.9 |
| 12 | 28.2 | 30.4 | 25.2 | 26.2 | 25.7 |

Example 7

Diffusion of Enzymes Through Cover Membranes Covered by a Hydrophilic Polymer

The percentage of activity of an enzyme solution passing through PETP cover membranes (coated with hydrophilic polyurethane and uncoated) was determined (Table B). It was shown that the membranes coated with a hydrophilic polyurethane effectively block migration of enzymes, thereby improving the linearity, the lifetime and sample-to-sample sensitivity of enzyme sensors having such coated cover membranes.

TABLE B

|  | Uncoated | PUR-coated |
|---|---|---|
| GOD | 99% | −1% |
| LOD | 100% | 0% |
| Urease | 103% | 0% |

Example 8

Preparation of Cover Membrane for Conventional Enzyme Sensor

Hydrophilic poly(meth)acrylates were prepared as follows using the amounts of starting materials described in Table C.

Methylmethacrylate (MMA), ethylacrylat (EA), and methoxy poly(ethyleneoxide) monomethacrylate (M-PEG-MMA; Aldrich #44,795-1) (amounts from Table D), 12.5 mg 2,2'-azobisisobutyronitrile and 12.5 mL ethoxyethyl acetate were mixed in a round-bottomed flask under stirring. The solution was flushed with nitrogen for 15 min. The flask was heated at 75° C. for 24 hours, and the solution was then cooled to room temperature. The viscous solution was diluted with 12.5 ml acetone, and the polymer was precipitated by pouring the solution into 375 mL hexane. The polymer was filtered off and redissolved in 25 mL acetone. The polymer was re-precipitated in 375 mL hexane and was allowed to stand for 16 hours in 125 mL hexane. The polymer was collected by filtration and dried for 16 hours at 50° C. in a vacuum oven.

TABLE C

|  | MMA Grams [mole %] | EA Grams [mole %] | M-PEG-MMA Grams [mole %] | Approx PEG amount % | Water absorption (estimated)/measured % |
|---|---|---|---|---|---|
| A (L555-1) | 3.14 [70] | 1.27 [28] | 1.08 [2] | 16 | (10)/17 |
| B (L555-2) | 3.15 | 1.88 | 1.92 | 24 | (38)/39 |
| C (L555-3) | 3.14 | 2.50 | 2.62 | 28 | (50)/47 |
| D (L555-4) | 3.13 [53] | 2.51 [42] | 3.42 [4.8] | 32 | (>100%)/60 |

A diffusion limiting porous membrane of an approximately 12 μm layer of polyethylene-therephthalate (PETP) (pore diameter approximately 0.1 μm; pore density: $3 \cdot 10^7$ pores/cm$^2$) was impregnated with a hydrophilic poly(meth)acrylate (polymers A-D; see Table D) by fully immersing sheets of a size of 150*200 mm in a 1% solution of the poly(meth)acrylate in 96% EtOH. After 5 seconds, the membrane was removed from the solution at a constant speed of around 50 mm/s. Afterwards, the membrane was allowed to dry until the ethanol had evaporated (less than 30 minutes). The sheets were subsequently cut into suitable pieces, where necessary.

The apparent diffusion coefficients of the membranes were as outlined in Table D.

TABLE D

| Membrane coated with polymer | Apparent diffusion coefficient cm$^2$/s |
|---|---|
| A (L555-1) | $1.35 \cdot 10^{-8}$ |
| B (L555-2) | $6.15 \cdot 10^{-9}$ |
| C (L555-3) | $4.56 \cdot 10^{-9}$ |
| D (L555-4) | $9.62 \cdot 10^{-9}$ |
| Uncoated | $1.73 \cdot 10^{-8}/1.56 \cdot 10^{-8}$ |

It appears from Table D that the diffusion properties for the membranes coated with hydrophilic polymers of the (meth)acrylate type are comparable with the diffusion properties of the membranes coated with hydrophilic polymers of the polyurethane type (see FIG. 6) taking into account the difference in pore densities.

Example 9

Exemplary Creatine and Creatinine Sensor Constructions

Creatinine and creatine sensors were prepares as in Example 2, with the exception that the diffusion limiting porous polymeric material 26 was prepared as described in Example using hydrophilic poly(meth)acrylates A (L555-1) and D (L555-4)

Example 10

Results For Creatine and Creatinine Sensors

Figure 11:
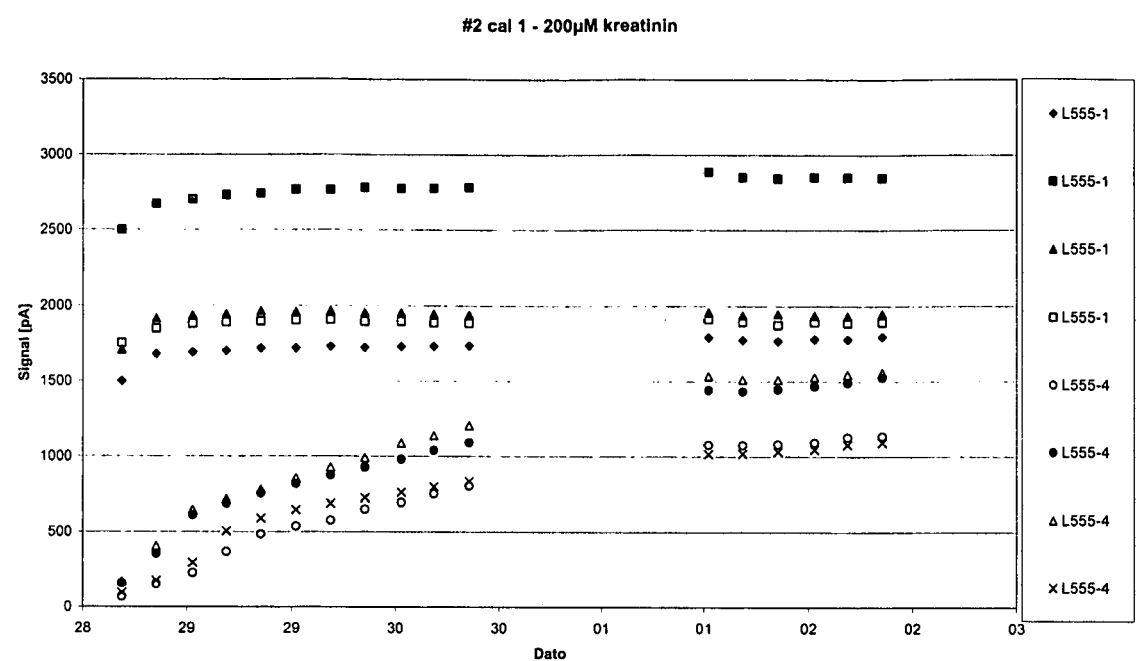
FIG. 11 illustrates the sensor response for a creatinine sensor covered with two types of hydrophilic poly(meth)acrylates exposed to a calibration solution comprising 200 μM of creatinine.

The two types of creatinine sensors prepared in Example 9 were tested (2×4 sensors) and the sensitivity to creatinine was measured. Sensors having a cover layer of hydrophilic poly(meth)acrylate A (L555-1) obtained the desired sensitivity within a few hours, whereas the sensors having a cover layer of hydrophilic poly(meth)acrylate A (L555-4) had a somewhat slower "start-up", see FIG. 11.

The invention claimed is:

1. An enzyme sensor for determining the concentration of an analyte in a fluid sample, comprising
   an electrode,
   at least one enzyme layer and
   a cover membrane layer for the at least one enzyme layer,
   wherein the cover membrane comprises at least one porous polymeric material having an average pore size in the range of 10 to 250 nm and a pore density in the range of $4 \times 10^4$ to $4 \times 10^7$ pores per cm$^2$,
   wherein the outer surface and pore mouths of at least one face of the cover membrane are covered by a continuous layer of a hydrophilic polymer extending over the outer surface and pore mouths, and
   wherein the hydrophilic polymer is selected from hydrophilic polyurethanes and hydrophilic poly(meth)acrylates having a water content when wetted in the range of 10 to 95% (w/w).

2. The enzyme sensor according to claim 1, wherein the at least one porous polymeric material of the cover membrane layer is at least partly impregnated with the hydrophilic polymer.

3. The enzyme sensor according to claim 1, wherein the at least one porous polymeric material is track-etched.

4. The enzyme sensor according to claim 1, wherein the hydrophilic polymer is selected from hydrophilic polyurethanes.

5. The enzyme sensor according to claim 4, wherein the hydrophilic polyurethanes are selected from aliphatic polyether urethanes, aliphatic polyether urethaneureas, cycloaliphatic polyether urethanes, cycloaliphatic polyether urethaneureas, aromatic polyether urethanes, aromatic polyether urethaneureas, aliphatic polyester urethanes, aliphatic polyester urethaneureas, cycloaliphatic polyester urethanes, cycloaliphatic polyester urethaneureas, aromatic polyester urethanes, and aromatic polyester urethaneureas.

6. The enzyme sensor according to claim 1, wherein the hydrophilic polymer is selected from hydrophilic poly(meth) acrylates.

7. The enzyme sensor according to claim 1, wherein the cover membrane layer is in a wet form and has a thickness in the range of about 5 to about 40 μm when the sensor is a conventional sensor.

8. The enzyme sensor according to claim 1, wherein the cover membrane layer is in a wet form and has a thickness in the range of about 1 to about 20 μm when the sensor is a planar sensor.

9. The enzyme sensor according to claim 1, wherein the hydrophilic polymer layer of the cover membrane is in a dry form and has a thickness of in the range of about 100 to about 2,000% of the average size of the pores of the at least one porous polymeric material.

10. The enzyme sensor according to claim 1, wherein the hydrophilic polymer layer of the cover membrane is in a dry form and has a thickness of in the range of about 0.1 to about 5 μm.

11. The enzyme sensor according to claim 1, wherein the cover membrane is in a dry form or a wet form and the ratio between the thickness of the cover membrane in the wet form and the thickness of the cover membrane in the dry form is in the range of about 2:1 to about 1:1.

12. The enzyme sensor according to claim 1, wherein the cover membrane is in a dry form or a wet form and the ratio between the thickness of the hydrophilic polymer layer of the cover membrane in the wet form and the thickness of the hydrophilic polymer layer of the cover membrane in the dry form is in the range of about 100:1 to about 1:1.

13. The enzyme sensor according to claim 1, wherein the weight ratio between the at least one porous polymeric material and the hydrophilic polymer when the hydrophilic polymer is in a non-wetted form is in the range of about 100:1 to about 1:1.

14. The enzyme sensor according to claim 1, wherein the cover membrane is the outermost layer of the sensor.

15. The enzyme sensor according to claim 1, wherein the at least one porous polymeric material is selected from polyethylene terephthalate, polyvinyl chloride, polycarbonate and mixtures thereof.

16. The enzyme sensor according to claim 1 further comprising 1 to 3 layers separating the electrode and the at least one enzyme layer.

17. A method of cleaning the enzyme sensor according to claim 1, the method comprising the step of contacting the surface of the cover membrane with a cleaning solution comprising a protease.

18. An enzyme sensor for determining the concentration of creatine in a fluid sample, comprising
a metal electrode,
a water-containing porous spacer layer in contact with the metal electrode,
an interference limiting layer in contact with the porous spacer layer,
an enzyme layer comprising sarcosine oxidase and creatinase in contact with the interference limiting layer, and
a cover membrane layer for the enzyme layer,
wherein the cover membrane layer comprises a porous polyethylene terephthalate material, and
wherein the outer surface and pore mouths of at least one face of the cover membrane are covered by a continuous layer of a hydrophilic polyurethane extending over the outer surface and pore mouths, wherein the hydrophilic polyurethane comprises backbone segments of polyethylene glycol in a weight ratio of polyethylene glycol segments of at least about 5% (w/w) and/or have a water content when wetted of at least about 25% (w/w).

19. An enzyme sensor for determining the concentration of creatinine in a fluid sample, comprising
a metal electrode,
a water-containing porous spacer layer in contact with the metal electrode,
an interference limiting layer in contact with the porous spacer layer,
an enzyme layer comprising sarcosine oxidase, creatininase and creatinase in contact with the interference limiting layer, and
a cover membrane layer for the enzyme layer,
wherein the cover membrane layer comprises a porous polyethylene terephthalate material, and
wherein the outer surface and pore mouths of at least one face of the cover membrane are covered by a continuous layer of a hydrophilic polyurethane extending over the outer surface and pore mouths, wherein the hydrophilic polyurethane comprises backbone segments of polyethylene glycol in a weight ratio of polyethylene glycol segments of at least about 5% (w/w) and/or have a water content when wetted of at least about 25% (w/w).

20. An enzyme sensor for determining the concentration of lactate in a fluid sample, comprising
a metal electrode,
an interference limiting layer in contact with the metal electrode,
an enzyme layer comprising lactate oxidase in contact with the interference limiting layer, and
a cover membrane layer for the enzyme layer,
wherein the cover membrane layer comprises a porous polyethylene terephthalate material, and
wherein the outer surface and pore mouths of at least one face of the cover membrane are covered by a continuous layer of a hydrophilic polyurethane extending over the outer surface and pore mouths, wherein the hydrophilic polyurethane comprises backbone segments of polyethylene glycol in a weight ratio of polyethylene glycol segments of at least about 5% (w/w) and/or have a water content when wetted of at least about 25% (w/w).

21. An enzyme sensor for determining the concentration of glucose in a fluid sample, comprising
a metal electrode,
an interference limiting layer in contact with the metal electrode,
an enzyme layer comprising glucose oxidase in contact with the interference limiting layer, and
a cover membrane layer for the enzyme layer,
wherein the cover membrane layer comprises a porous polyethylene terephthalate material, and wherein the outer surface and pore mouths of at least one face of the cover membrane are covered by a continuous layer of a hydrophilic polyurethane extending over the outer surface and pore mouths, wherein the hydrophilic polyurethane comprises backbone segments of polyethylene glycol in a weight ratio of polyethylene glycol segments of at least about 5% (w/w) and/or have a water content when wetted of at least about 25% (w/w).

22. An apparatus for determining the concentration of an analyte in a fluid sample, comprising one or more enzyme sensors as defined in any one of the claims 1, 18, 19, 20 and 21.

23. A method of determining the concentration of an analyte in a fluid sample, comprising the steps of contacting the fluid sample with an enzyme sensor according to any one of the claims 1, 18, 19, 20 and 21, and conducting at least one measurement involving the electrode of the enzyme sensor.

* * * * *